US009771423B2

(12) United States Patent
Ghezzi et al.

(10) Patent No.: US 9,771,423 B2
(45) Date of Patent: Sep. 26, 2017

(54) ANTI-VCAM-1 NANOBODIES

(75) Inventors: Catherine Ghezzi, Grenoble (FR); Daniel Fagret, Grenoble (FR); Alexis Broisat, Grenoble (FR); Nick Devoogdt, Zemst (BE); Tony Lahoutte, Ganshoren (BE); Serge Muydermans, Hoeilaart (BE)

(73) Assignees: VIRJE UNIVERSITEIT BRUSSEL, Brussel (BE); CENTRE HOSPITALIER UNIVERSITAIRE DE GRENOBLE, La Tronche (FR); UNIVERSITE GRENOBLE ALPES, Saint Martin D'Heres (FR)

( * ) Notice: Subject to any disclaimer, the term of this patent is extended or adjusted under 35 U.S.C. 154(b) by 579 days.

(21) Appl. No.: 14/240,340

(22) PCT Filed: Aug. 22, 2012

(86) PCT No.: PCT/EP2012/066348
§ 371 (c)(1),
(2), (4) Date: May 2, 2014

(87) PCT Pub. No.: WO2013/026878
PCT Pub. Date: Feb. 28, 2013

(65) Prior Publication Data
US 2014/0255303 A1 Sep. 11, 2014

(30) Foreign Application Priority Data
Aug. 23, 2011 (FR) ...................................... 11 57478

(51) Int. Cl.
A61K 39/395 (2006.01)
C07K 16/28 (2006.01)
A61K 51/10 (2006.01)
G01N 33/68 (2006.01)
(52) U.S. Cl.
CPC ...... *C07K 16/2803* (2013.01); *A61K 51/1027* (2013.01); *C07K 16/2836* (2013.01); *G01N 33/6893* (2013.01); *C07K 2317/22* (2013.01); *C07K 2317/33* (2013.01); *C07K 2317/565* (2013.01); *C07K 2317/569* (2013.01); *C07K 2317/92* (2013.01); *C07K 2317/94* (2013.01)
(58) Field of Classification Search
None
See application file for complete search history.

(56) References Cited

U.S. PATENT DOCUMENTS

2009/0208408 A1 8/2009 Boturyn et al.
2011/0200533 A1 8/2011 Port et al.

FOREIGN PATENT DOCUMENTS

| EP | 1 520 588 A2 | 4/2005 |
| EP | 2 206 726 A1 | 7/2010 |
| FR | 2 876 033 A1 | 4/2006 |
| FR | 2 914 304 A1 | 10/2008 |

OTHER PUBLICATIONS

Written Opinion of the International Searching Authority for the corresponding PCT/EP2012/0663348, filed Aug. 22, 2012 (English translation of the Written Opinion of the International Search Authority Feb. 23, 2014).*
Rudikoff et al., Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Broisat et al., Cellular and Molecular Immunology, VUB, Brussels, Belgium. Molecular Imaging and Biology, Feb. 2012, 14: Suppl 1, p. S829, Abstract No. TO67. Meeting Info.: 2011 World Molecular Imaging Congress, WMIC 2011 San Diego, CA USA, Sep. 2011.*
Behm, C.Z. et al. 2008 "Molecular imaging of endothelial vascular cell adhesion molecule-1 expression and inflammatory cell recruitment during vasculogenesis and ischemic-mediated arteriogensis" *Circulation* 117:22, 2902-2911.
Broisat, A. et al. 2007 "Molecular imaging of vascular cell adhesion molecule-1 expression in experimental atherosclerotic plaques with radiolabelled B2702-p" *European Journal of Nuclear Medicine and Molecular Imaging* 34: 830-840.
Broisat, A. et al. 2009 "Imagerie moleculaire de plaque d'atherome vulnerable. Evaluation preclinique et Clinique de traceurs radioactifs" *Medecine Nucleaire* 33: 128-136.
Broisat, A. et al. 2012 "Nanobodies targeting Mouse/human VCAM1 for the nuclear imaging of atherosclerotic lesions" *Circulation Research* 110: 927-937.
De Groeve, K. et al. 2010 "Nanobodies as tools for in vivo imaging of specific immune cell types" *Journal of Nuclear Medicine* 51: 782-789.
Dimastromatteo, J. et al. 2009 "In vivo molecular imaging of vascular cell adhesion molecule-1 expression in atherosclerotic plaques" *Archives of Cardiovascular Disease* 102, 1 page (Abstract).
Hernot, S. et al. 2012 "Nanobody-coupled microbubbles as novel molecular tracer" *Journal of Controlled Release* 158: 346-353.
Kaufmann, B.A. et al. 2007 "Molecular imaging of inflammation in atherosclerosis with targeted ultrasound detection of vascular cell adhesion molecule-1" *Circulation* 116: 276-284.
Kelly, K.A. et al. 2005 "Detection of vascular adhesion molecule-1 expression using a novel multimodal nanoparticle" *Circulation Research* 16: 327-336.
Nahrendorf, M. et al. "Noninvasive vascular cell adhesion molecule-1 imaging identifies inflammatory activation of cells in atherosclerosis" *Circulation* 114: 1504-1511.
Riou, L.M. et al. 2009 "Pre-clinical and Clinical evaluation of nuclear tracers for the molecular imaging of vulnerable atherosclerosis: an Overview" *Current Medicinal Chemistry* 16: 1499-1511.
Vaneycken, I. et al., 2011 "Immuno-imaging using nanobodies" *Current Opinion in Biotechnology* 22: 877-881.

* cited by examiner

*Primary Examiner* — Phillip Gambel
(74) *Attorney, Agent, or Firm* — Knobbe, Martens Olson & Bear, LLP

(57) ABSTRACT

The present invention relates to nanobodies specifically directed against VCAM-1 and to their use in medical imaging and in diagnostic, prognostic and treatment methods.

14 Claims, 16 Drawing Sheets

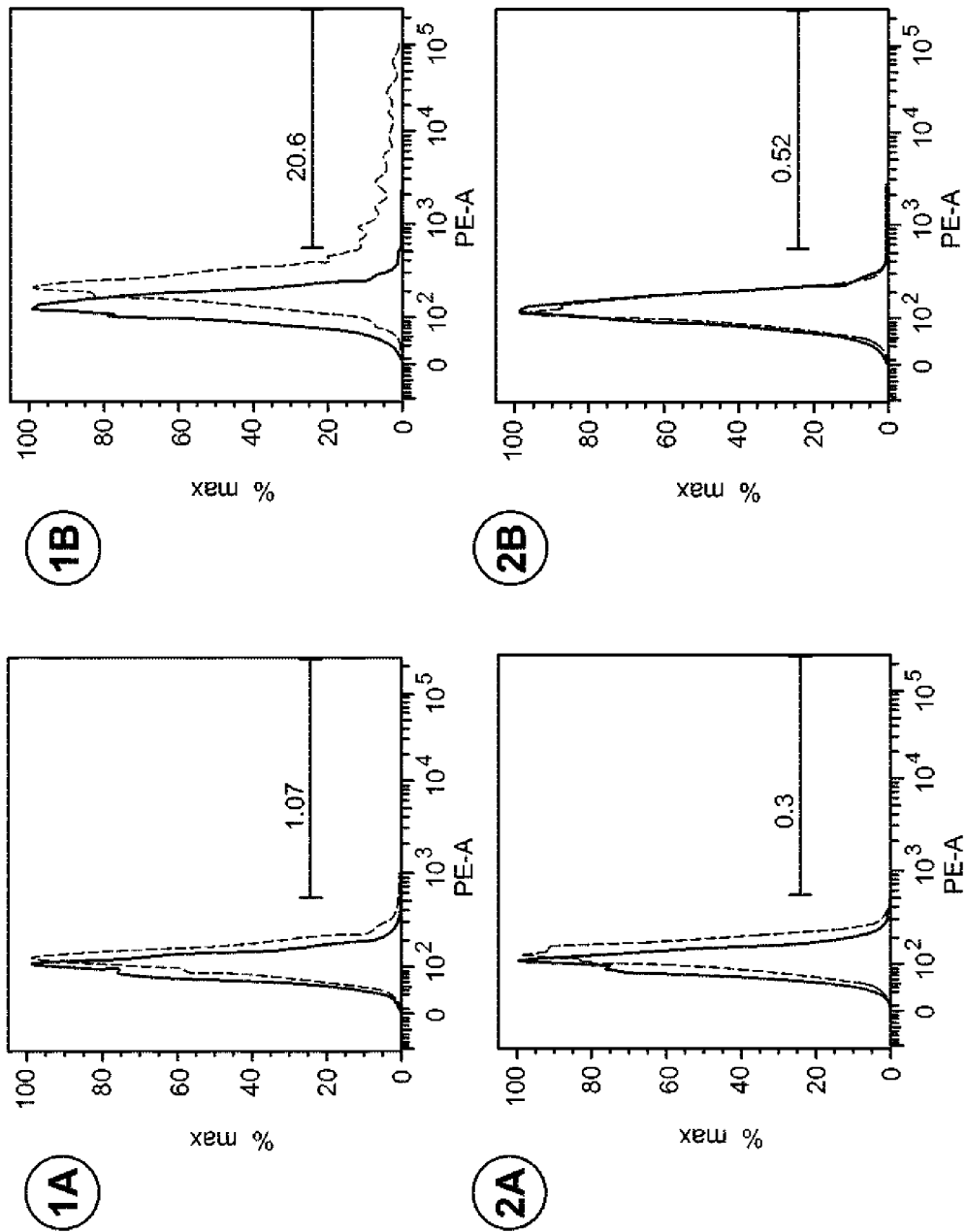
FIG. 11 (Start)

ANTI-VCAM-1 NANOBODIES

FIELD OF THE INVENTION

The present invention relates to anti-VCAM-1 nanobodies allowing detection in vivo of atheroma plaques.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 17321330_1.TXT, the date of creation of the ASCII text file is Feb. 21, 2014, and the size of the ASCII text file is 16.7 KB.

BACKGROUND OF THE INVENTION

Cardiovascular diseases represent the worldwide leading cause of mortality and coronary disease is responsible by itself for more than half of these deaths. The onset of a coronary event is due, in the vast majority of cases, to the disruption of a vulnerable coronary atheroma plaque. Coronagraphy, a present standard technique for diagnosing the coronary disease, does not allow identification of non-stenosing plaques.

Nuclear imaging obviously has significant advantages for molecular imaging of the vulnerable atheroma plaque. Many tracers, of diverse chemical natures, among which lipoproteins, peptides, oligopeptides, antibodies, sugars, antisense nucleotides and nanoparticles, have been evaluated experimentally for molecular imaging (Riou et al. (2009) Curr. Med. Chem. 16:1499-1511). The main evaluated targets have been oxidized LDLs and their receptors, the inflammatory phenomenon via cell imaging of macrophages, or imaging of receptors of enzymes expressed by this cell type, the apoptotic phenomenon and the neo-angiogenic phenomenon. Among the tracers targeting the inflammatory process, $^{99m}$Tc-MCP-1 for nuclear imaging in the SPECT (Single Photon Emission Computed Tomography) mode and [$^{18}$F]-FDG for the PET (Positron Emission Tomography) method have allowed non-invasive in vivo imaging of the accumulation of macrophages in experimental atherosclerotic lesions. On a clinical level, [$^{18}$F]-FDG and $^{99m}$Tc-Annexin A5 have allowed non-invasive imaging of the accumulation of macrophages and of apoptotic cells, respectively in carotidian atheroma plaques of symptomatic patients. However, none of these radiotracers are presently used in clinical practice systematically, mainly because of their incapacity of attaining sufficient lesions-to-background-noise ratios at coronary lesions. Indeed, nuclear imaging of the vulnerable plaques at the coronary arteries is particularly difficult because of the small volume of the lesions and of their proximity with the blood which contains an unbound circulating tracer. Therefore, no clinical test exists at the present time showing the feasibility of imaging of coronary atheroma.

VCAM-1 is a glycoprotein from the family of immunoglobulins, the expression of which is induced in a pro-atherogenic condition. Its expression is restricted to the areas of development of atheroma plaques and it lasts during the totality of the development of the vulnerable plaque. The role of VCAM-1 is to ensure the recruitment of inflammation cells (lymphocytes and monocytes) towards the plaque. The expression of VCAM-1 is therefore directly correlated with the accumulation of macrophages, which is recognized as one of the major criteria in the definition of a vulnerable plaque (Naghavi et al. (2003) Circulation 108:1772-1178). The present inventors have previously developed radiotracers containing a peptide sequence capable of binding to VCAM-1. They have shown on an atherosclerotic rabbit model that the binding of this radiotracer on autoradiographic images ex vivo was correlated with the areas of development of atheroma plaques and with the expression of VCAM-1 (Broisat et al. (2007) Eur. J. Nucl. Med. Mol. Imaging 34:830-840). However, because of the circulating blood activity of this tracer, it is not possible to use it in vivo in medical imaging.

Indeed, in a general way, the signal to noise ratio should be high in order to produce quality medical imaging. An ideal radiotracer is therefore characterised by high affinity and specificity for its target, good solubility and stability, efficient radiolabeling, a small size as well as by rapid removal from the blood, so that images with a high contrast level may be rapidly obtained after administration of the tracer. This is most particularly crucial in the case of the atheroma plaque because of its small size and of its intravascular localisation.

SUMMARY OF THE INVENTION

The present invention results from the discovery by the inventors that four nanobodies, called cAbVCAM1-5, cAbVCAM1-3, cAbVCAM1-8 and cAbVCAM1-9, comprising specific CDR sequences, surprisingly had and unlike other nanobodies binding to VCAM-1, all the features defined above and were therefore efficient radiotracers for non-invasive medical imaging of atheroma plaques, in particular coronary atheroma plaques.

The object of the present invention is therefore a nanobody directed against VCAM-1 comprising:
  a) the amino acid sequences (i) YTNSIMYMA (SEQ ID NO: 1) as CDR1, (ii) AIRFPDDS (SEQ ID NO: 2) as CDR2 and (iii) RSSPYSFAWNDPSNYNY (SEQ ID NO: 3) as CDR3; or
  b) the amino acid sequences (i) FTYSSYYMS (SEQ ID NO: 4) as CDR1, (ii) GINVDGSN (SEQ ID NO: 5) as CDR2 and (iii) GSGRDSYDCYSGSWCP (SEQ ID NO: 6) as CDR3; or
  c) the amino acid sequences (i) FTFSNYYMT (SEQ ID NO: 7) as CDR1, (ii) RINSDGS (SEQ ID NO: 8) as CDR2 and (iii) GKSSV (SEQ ID NO: 9) as CDR3; or
  d) the amino acid sequences (i) FTFSSYYMS (SEQ ID NO: 10) as CDR1, (ii) GINVDGSN (SEQ ID NO: 11) as CDR2 and (iii) GSGRDSYDCYSGSWCP (SEQ ID NO: 12) as CDR3;
or a functionally conservative variant of the nanobody defined in a), b), c) or d) comprising a conservative substitution of one or two amino acids in one, two or three of the sequences respectively SEQ ID NO: 1, SEQ ID NO: 2 and SEQ ID NO: 3, or SEQ ID NO: 4, SEQ ID NO: 5 and SEQ ID NO: 6, or SEQ ID NO: 7, SEQ ID NO: 8 and SEQ ID NO: 9, or SEQ ID NO: 10, SEQ ID NO: 11 and SEQ ID NO: 12.

The present invention also relates to the nanobody as defined above for its use as a contrast agent in non-invasive, in vivo medical imaging, for its use in diagnostic or prognostic methods and for its use as a drug.

The object thereof is also the use of this nanobody for in vitro detection of VCAM-1 in a sample.

Finally it relates to a pharmaceutical composition comprising this nanobody associated with a pharmaceutically acceptable carrier.

BRIEF DESCRIPTION OF THE DRAWINGS

The present invention will be illustrated in more detail by the figures and examples below.

DETAILED DESCRIPTION OF THE PREFERRED EMBODIMENT

VCAM-1

Figure 1:
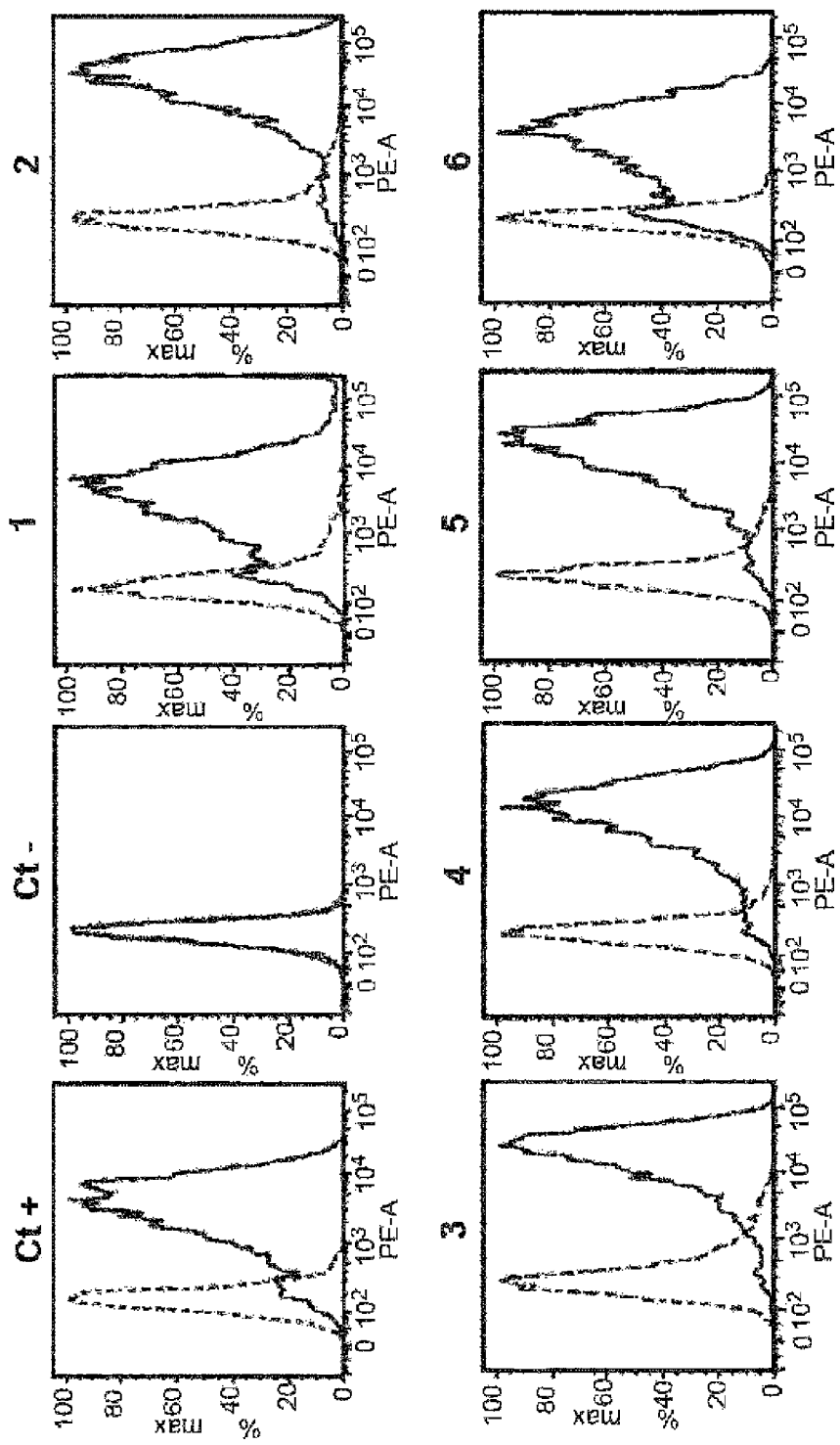
FIG. 1 shows the flow cytometry analysis of anti-VCAM-1 nanobodies (cAbVCAM1-1: 1; cAbVCAM1-2: 2; cAbVCAM1-3: 3; cAbVCAM1-4: 4; cAbVCAM1-5: 5; cAbVCAM1-6: 6; cAbVCAM1-7: 7; cAbVCAM1-8: 8; cAbVCAM1-9: 9 and cAbVCAM1-10: 10) on untreated bEND5 mouse cells (dotted line) or treated with TNFα (solid line). A mouse anti-VCAM-1 monoclonal antibody marked with PE (Ct+) was used as a positive control and the nanobody cAbBcII10 (Ct−) was used as a negative control.
Figure 1:
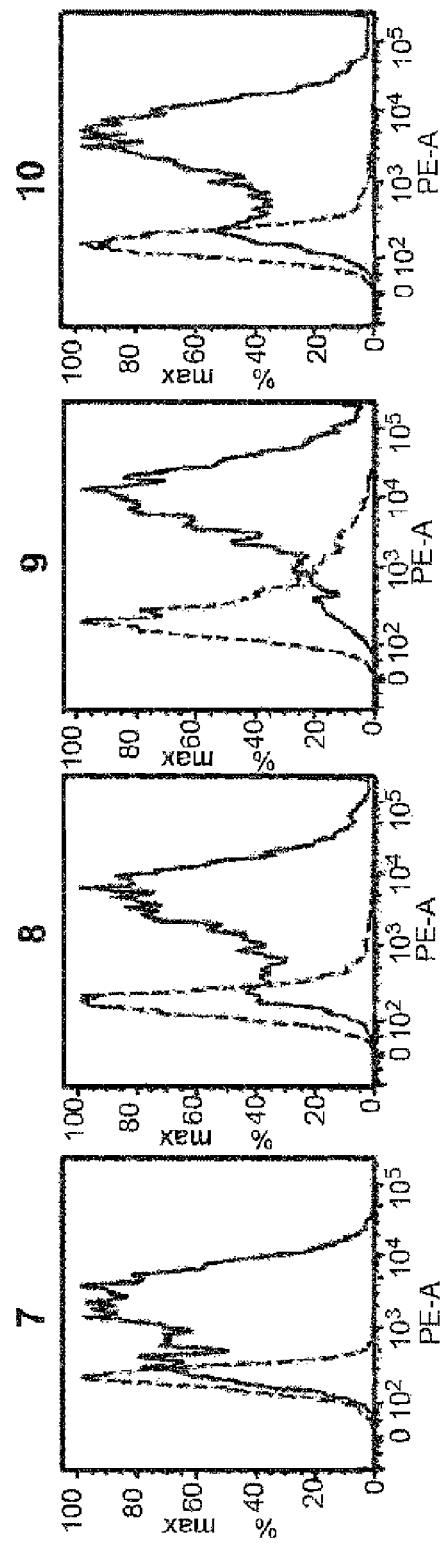

The term "VCAM-1" or "vascular cell adhesion molecule 1" designates a protein for cell adhesion, the transcription of which is induced in endothelial cells but is also expressed by other cell types. VCAM-1 was discovered and cloned by Osborn et al. in 1989 (Osborn et al. (1989) *Cell*. 59:1203-1211). VCAM-1 interacts with α4β1 integrin also called VLA-4 (Very Late Antigen 4), which is constitutively expressed by lymphocytes and monocytes, notably. Like other adhesion molecules, such as ICAM-1, 2 and 3, VCAM-1 is involved in the adhesion of monocytes to the endothelium during atherosclerosis. VCAM-1 also interacts with α4β7 integrin for recruiting lymphocytes at the intestine.

Anti-VCAM-1 Nanobodies

In the context of the present invention, the terms of "antibody" and "immunoglobulin" have the same meaning and are used indifferently. In conventional antibodies, the two heavy chains are bound to each other through disulfide bridges and each heavy chain is bound to a light chain through a disulfide bridge. There are two types of light chain: lambda (λ) and kappa (κ) light chains. There exist five main classes of heavy chains (or isotypes) which determine the functional activity of an antibody: IgM, IgD, IgG, IgA and IgE. Each chain contains distinct sequence domains. The light chain comprises two domains: a variable domain (VL) and a constant domain (CL). The heavy chain comprises four domains: a variable domain (VH) and three constant domains (CH1, CH2 and CH3, collectively designated as CH). The variable regions of the heavy chains (VH) and light chains (VL) determine the recognition of a bond and the specificity to the antigen. The domains of the constant regions of the light (CL) and heavy (CH) chains give important biological properties such as the association of the chains of the antibodies, secretion, transplacental mobility, the bond to the complement and the bond to Fc receptors. The fragment Fv is the N-terminal portion of the Fab fragment of an immunoglobulin consisting of variable portions of a light chain and of a heavy chain. The specificity of the antibody lies in the structural complementarity between the combination site of the antibody and the antigenic determinant. The combination sites of the antibody are made of residues which mainly stem from hypervariable regions or regions for determining complementarity (CDRs). Occasionally, residues from non-hypervariable regions or "framework" regions (FR) may influence the global structure of the domain and therefore the combination site.

Within the context of the invention, the term "CDR" refers to the sequences of amino acids, which together define the bond affinity and the specificity of the natural Fv region of a native binding site of an immunoglobulin. The heavy and light chains of an immunoglobulin each have three CDRs, designated as H-CDR1, H-CDR2, H-CDR3 and L-CDR1, L-CDR2, L-CDR3 respectively. A site for binding to the antigen therefore includes the 6 CDRs, comprising the whole of the CDRs of a variable region of a heavy chain and of a variable region of a light chain.

The localization of the CDRs in the sequence of an antibody or a nanobody may be determined by one skilled in the art by using techniques described earlier. Typically, the CDRs may be identified by sequencing the DNA of the antibody or of the nanobody with a suitable system, such as the 3730XL DNA Analyzer and ABI PRISM BigDye® Terminator cyc, and then by analyzing the thereby obtained sequences by means of dedicated databases such as the international ImMunoGeneTics Information System® or IMTG® (Lefranc (2003) *Dev. Comp. Immunol.* 27:55).

Within the context of the invention, the terms of "framework region", 'framework' or "FR", refer to amino acid sequences inserted between the CDRs.

Within the context of the invention, the terms of "nanobody", "VHH", "VHH antibody fragment" and "single domain antibody" are used indifferently and designate the variable domain of the single heavy chain of antibodies of the type of those found in *Camelidae*, which are naturally without any light chains. In the absence of a light chain, the nanobodies each have three CDRs, designated as CDR1, CDR2 and CDR3 respectively. The nanobodies according to the invention may in particular be nanobodies of camels, dromedaries, llamas or alpacas. Preferably, the nanobodies according to invention are nanobodies of dromedaries.

By "nanobody directed against VCAM-1", is meant here a nanobody capable of selectively binding to VCAM-1. Preferentially, the nanobody is specific of VCAM-1, i.e. it binds to VCAM-1 excluding any other molecule.

The present inventors have more specifically identified four nanobodies directed against the VCAM-1 and having unexpected additional features which other anti-VCAM-1 nanobodies do not have. Indeed, these four nanobodies, cAbvCAM1-5, cAbVCAM1-3, cAbVCAM1-8, cAbVCAM1-9, have a cross-reaction for human and murine VCAM-1; they have very strong affinity for murine or human VCAM-1, and they bind very strongly in the atheroma plaques in vivo, without, however, inducing background noise in the organs of the patient.

These four nanobodies were sequenced:
The nanobody cAbVCAM1-5 has the amino acid sequence QVQLQESGGGSVQTGGSLRLSCAAS-GYTNSIMYMAWFRQAPGKKREGVA AIRF-PDDSAYYAGSVKGRFTISHDNAKNTVYLQMNN-LNPEDTAMYYCAAR SSPYSFAWNDPSNYNYWGQGTQVTVSS (SEQ ID NO: 13),
The nanobody cAbVCAM1-3 has the amino sequence cAbVCAM1-3 QVQLQESGGGSVQAGGSL-RLSCTASGFTYSSYYMSWVRQAPGKGLEWV SGINVDGSNTYYADSVKGRFTISRDNAKNT-LYLQMNSLKSEDTALYYCATG SGRDSYD-CYSGSWCPKGQGTQVTVSS (SEQ ID NO: 14),
The nanobody cAbVCAM1-8 has the amino acid sequence QVQLQESGGGLVQPGGSLRLSCAAS-GFTFSNYYMTWVRRAPGKGLEWV SRINSDGST-LYLPSVKGRFTISRDNAKNTLYLQMNSLKSEDT-GWYYCVEGK SSVRGQGTQVTVSS (SEQ ID NO: 15), and
The nanobody cAbVCAM1-9 has the amino acid sequence QVQLQESGGGLVQPGGSLRLSCAAS-GFTFSSYYMSWVRQAPGKGLEWV SGINVDG-SNTYYADSVKGRFTISRDNAKNT-LYLQMNSLKSEDTALYYCATG SGRDSYDCYSGSWCPKGQGTQVTVSS (SEQ ID NO: 16).

The CDRs of these four nanobodies were more specifically sequenced and are the following:

```
cAbVCAM1-5
                                        (SEQ ID NO: 1)
CDR1: YTNSIMYMA (SEQ ID NO: 2)
CDR2: AIRFPDDS (SEQ ID NO: 3)
CDR3: RSSPYSFAWNDPSNYNY cAbVCAM1-3
                                        (SEQ ID NO: 4)
CDR1: FTYSSYYMS (SEQ ID NO: 5)
CDR2: GINVDGSN (SEQ ID NO: 6)
CDR3: GSGRDSYDCYSGSWCP cAbVCAM1-8
                                        (SEQ ID NO: 7)
CDR1: FTFSNYYMT (SEQ ID NO: 8)
CDR2: RINSDGS (SEQ ID NO: 9)
CDR3: GKSSV cAbVCAM1-9
                                        (SEQ ID NO: 10)
CDR1: FTFSSYYMS (SEQ ID NO: 11)
CDR2: GINVDGSN
```

```
                                                 (SEQ ID NO: 12)
CDR3: GSGRDSYDCYSGSWCP
```

As this is well known to one skilled in the art, the combination of the CDR1, CDR2 and CDR3 is sufficient for defining a site for binding to the antigen. Therefore, an object of the present invention relates to a nanobody directed against VCAM-1 comprising:

a) the amino acid sequences (i) SEQ ID NO: 1 as CDR1, (ii) SEQ ID NO: 2 as CDR2 and (iii) SEQ ID NO: 3 as CDR3; or b) the amino acid sequences (i) SEQ ID NO: 4 as CDR1, (ii) SEQ ID NO: 5 as CDR2 and (iii) SEQ ID NO: 6 as CDR3; or c) the amino acid sequences (i) SEQ ID NO: 7 as CDR1, (ii) SEQ ID NO: 8 as CDR2 and (iii) SEQ ID NO: 9 as CDR3; or d) the amino acid sequences (i) SEQ ID NO: 10 as CDR1, (ii) SEQ ID NO: 11 as CDR2 and (iii) SEQ ID NO: 12 as CDR3;

or a functionally conservative variant of the nanobody defined in a), b), c) or d) comprising a conservative substitution of one or two amino acids in one, two or three of the sequences respectively SEQ ID NO: 1, SEQ ID NO: 2 and SEQ ID NO: 3, or SEQ ID NO: 4, SEQ ID NO: 5 and SEQ ID NO: 6, or SEQ ID NO: 7, SEQ ID NO: 8 and SEQ ID NO: 9, or SEQ ID NO: 10, SEQ ID NO: 11 and SEQ ID NO: 12.

The inventors also sequenced the "framework" regions (FR) of these nanobodies. The corresponding sequences are the following:

```
cAbVCAM1-5
                                                 (SEQ ID NO: 17)
Region FR1: QVQLQESGGGSVQTGGSLRLSCAASG (SEQ ID NO: 18)
Region FR2: WFRQAPGKKREGVA (SEQ ID NO: 19)
Region FR3:
AYYAGSVKGRFTISHDNAKNTVYLQMNNLNPEDTAMYYCAA (SEQ ID NO: 20)
Region FR4: WGQGTQVTVSS cAbVCAM1-3
                                                 (SEQ ID NO: 21)
Region FR1: QVQLQESGGGSVQAGGSLRLSCTASG (SEQ ID NO: 22)
Region FR2: WVRQAPGKGLEWVS (SEQ ID NO: 23)
Region FR3:
TYYADSVKGRFTISRDNAKNTLYLQMNSLKSEDTALYYCAT (SEQ ID NO: 24)
Region FR4: KGQGTQVTVSS cAbVCAM1-8
                                                 (SEQ ID NO: 25)
Region FR1: QVQLQESGGGLVQPGGSLRLSCAASG (SEQ ID NO: 26)
Region FR2: WVRRAPGKGLEWVS (SEQ ID NO: 27)
Region FR3:
TLYLPSVKGRFTISRDNAKNTLYLQMNSLKSEDTGWYYCVE (SEQ ID NO: 28)
Region FR4: RGQGTQVTVSS cAbVCAM1-9
                                                 (SEQ ID NO: 29)
Region FR1: QVQLQESGGGLVQPGGSLRLSCAASG (SEQ ID NO: 30)
Region FR2: WVRQAPGKGLEWVS (SEQ ID NO: 31)
Region FR3:
TYYADSVKGRFTISRDNAKNTLYLQMNSLKSEDTALYYCAT (SEQ ID NO: 32)
Region FR4: KGQGTQVTVSS
```

In a particular embodiment, the invention relates to a nanobody comprising or consisting in the chaining of sequences FR1-CDR1-FR2-CDR2-FR3-CDR3-FR4 as defined above of one of the nanobodies identified by the inventors.

Preferably, the nanobody according to the invention is therefore a nanobody comprising or consisting of a sequence of amino acids selected from the group consisting of the amino acid sequences SEQ ID NO: 13, SEQ ID NO: 14, SEQ ID NO: 15 and SEQ ID NO: 16, or a functionally conservative variant of the latter comprising a conservative substitution of one or two amino acids in one, two or three of the CDRs comprised in the sequence of amino acids respectively SEQ ID NO: 13, SEQ ID NO: 14, SEQ ID NO: 15 or SEQ ID NO: 16. The functionally conservative variant as defined above may further comprise of one or several substitutions, in particular one or several conservative substitutions in the regions of the amino acid sequences respectively SEQ ID NO: 16, SEQ ID NO: 14, SEQ ID NO: 15 or SEQ ID NO: 16 which are not CDRs, such as the "framework" regions, in particular the "framework" regions defined above. More preferably, the nanobody according to invention is a nanobody comprising or consisting of a sequence of amino acids selected from the group consisting of the amino acid sequences SEQ ID NO: 13, SEQ ID NO: 14, SEQ ID NO: 15 and SEQ ID NO: 16. Preferably, above all, the nanobody according to the invention is a nanobody, comprising or consisting of the sequence of amino acids SEQ ID NO: 13.

In the context of the invention, the expression "functionally conservative variant" refers to variants in which a given amino acid in a nanobody according to the invention is substituted without altering the global conformation and the function of the nanobody, including a replacement of an amino acid with another having similar properties (for example polarity, hydrogen bond potential, acidity, basicity, hydrophobicity, presence of an aromatic group, etc). The amino acids having similar properties are well known to one skilled in the art, for example arginine, histidine and lysine from hydrophilic-basic amino acids and may be interchangable. Similarly, isoleucine, a hydrophobic amino acid, may be replaced with leucine, methionine or valine. Such changes should have no or little effect on the apparent molecular weight or on the isoelectric point of the nanobody. A natural amino acid may be replaced with a non-natural amino acid, such as an amino acid in a D configuration, a beta or gamma amino acid.

Examples of conservative substitutions are shown in Table 1 below.

TABLE 1

Conservative Substitutions I

| Characteristic of the side chain | Amino acid |
|---|---|
| Non polar | G A P I L V |
| Polar not charged | C S T M N Q |
| Polar charged | D E K R |
| Aromatic | H F W Y |
| Other | N Q D E |

Alternatively, the conservative amino acids may be grouped as described in Lehninger (1975, Biochemistry, 2nd Edition, Worth Publishers, Inc. New-York: NY., p. 71-77), as shown in Table 2 below.

TABLE 2

Conservative substitutions II

| Characteristic of the side chain | | Amino acid |
|---|---|---|
| Non polar | Aliphatic | A L I V P |
| | Aromatic | F W |
| | Containing sulfur | M |
| | Boundary | G |
| Polar non-charged | Hydroxyl | S T Y |
| | Amides | N Q |
| | Sulfhydryl | C |
| | Boundary | G |
| Positively charged (basic) | | K R H |
| Negatively charged (acid) | | D E |

According to another alternative, examples of conservative substitutions conservatives are shown in Table 3 below.

TABLE 3

Conservative substitutions III

| Original residue | Substitution example |
|---|---|
| A | V L I |
| R | K Q N |
| N | Q H K R |
| D | E |
| C | S |
| G | N |
| E | D |
| H | N Q K R |
| I | L V M A F |
| L | I V M A F |
| K | R Q N |
| M | L F I |
| F | L V I A |
| P | G |
| S | T |
| T | S |
| W | Y |
| Y | W F T S |
| V | I L M F A |

These functionally conservative variants preserve their capability of binding VCAM-1. Preferentially, these functionally conservative variants have a bond affinity with VCAM-1 equal or increased relatively to the corresponding nanobody.

By knowing the amino acid sequence of the nanobody of interest, one skilled in the art is capable of producing the nanobodies according to the invention, in particular the nanobodies cAbVCAM1-5, cAbVCAM1-3, cAbVCAM1-8 and cAbVCAM1-9 defined above, by conventional techniques for producing polypeptides. For example, they may be synthesized by using a well known synthesis method in a solid phase (Merrifield (19962) *Proc. Soc. Ex. Boil.* 21:412; Merrifield (1963) *J. Am. Chem. Soc.* 85:2149; Tam et al. (1983) *J. Am. Chem. Soc.* 105:6442), preferably by using a commercial available peptide synthesis apparatus, (such as the one made by Applied Biosystems, Foster City, Calif.) and by following the instructions of the manufacturer.

Alternatively, the nanobodies according to the invention may be synthesized with recombinant DNA techniques well known one skilled in the art (Maniatis et al. (1982) Molecular Cloning: a laboratory manual, Cold Spring Harbor Laboratories, NY, 51-54 and 412-430). For example, they may be obtained as DNA expression products after incorporating DNA sequences coding for the polypeptide of interest in expression vectors and introducing these vectors in suitable prokaryotic or eukaryotic hosts which will express the polypeptide of interest, from which they may then be isolated by using techniques well known to one skilled in the art. As this is well known to one skilled in the art, when a protein is synthesized by recombinant DNA techniques, it is generally synthesized, associated with a label facilitating its purification. Such labels are well known to one skilled in the art and for example include hexahistidine (6His), glutathion-S-transferase (GST) or hemagglutinin of the influenza virus (HA). Preferably, the nanobodies according to the invention comprise a hexahistidine label. Therefore, an object of the invention is also formed by a nanobody comprising or consisting of the sequence of amino acids selected from the group formed by the sequences SEQ ID NO: 13, SEQ ID NO: 14, SEQ ID NO: 15 and SEQ ID NO: 16 further comprising at their C-terminal or N-terminal end, preferably at their C-terminal end, six histidine residues. A nanobody comprising or consisting of the sequence of amino acids selected from the group formed by sequences SEQ ID NO: 33, SEQ ID NO: 34, SEQ ID NO: 35 and SEQ ID NO: 36 is also therefore part of the invention.

Another object of the invention relates to a nucleic acid comprising a nucleic sequence coding for the nanobody according to the present invention.

In a particular embodiment, the nucleic acid according to the invention comprises or consists of a nucleic sequence coding for a nanobody defined by one of the sequences of amino acids SEQ ID NO: 13, SEQ ID NO: 14, SEQ ID NO: 15 or SEQ ID NO: 16. Preferably, the nucleic acid according to the invention comprises or consists of a nucleic sequence coding for the nanobody defined by the sequence of amino acids SEQ ID NO: 13.

Typically, said nucleic acid is a DNA or RNA molecule, which may be included in any suitable vector, such as a plasmid, a cosmid, an episome, an artificial chromosome, a phage or a viral vector.

The terms "vector", "cloning vector" and "expression vector" means the carrier by which the DNA or RNA sequence may be introduced into the host cell, so as to transform the host and promote expression (e.g. transcription and translation) of the introduced sequence.

Therefore, another object of the invention relates to a vector comprising a nucleic acid according to the invention.

Such vectors may comprise regulating elements such as a promoter, an activator, a terminator, etc, for causing or directing the expression of the polypeptide. Examples of promoters and activators used in the expression vectors for an animal cell include the early promoter and activator of SV40 (Mizukami et al. (1987) *J. Biochem.* 101:1307-1310), the promotor LTR and the activator of the leukemia virus of the Moloney mouse, the promoter (Mason et al (1985) *Cell*

41:479-487) and the activator (Gillies et al. (1983) *Cell* 33:717-728) of the immunoglobulin chain, etc.

Any expression vector for animal cells may be used. Examples of suitable vectors include pAGE 107 (Miyaji et al. (1990) *Cytotechnology* 3:133-140), pAGE 103 (Mizukami et al. (1987) *J. Biochem.* 101:1307-1310), pHSG274 (Brady et al. (1984) *Gene* 27:223-232), pKCR (O'Hare et al. (1981) *Proc. Natl. Acad. Sci. USA* 78:1527-1531), pSG1 beta d2-4 (Miyaji et al. (1990) *Cytotechnology* 3:133-140), etc.

Other examples of plasmids include replicating plasmids comprising a replication origin, or integrative plasmids such as for example pUC, pcDNA, pBR, etc.

Other examples of viral vectors include adenoviral, retroviral vectors, that of the herpes virus and AAV. Such recombinant viruses may be produced by techniques well known to one skilled in the art, such as by transfection of packaging cells or by transient transfection with auxiliary plasmids or viruses. Typical examples of virus packaging cells include the PA317 cells, the PsiCRIP cells, the GPenv+ cells, the 293 cells, etc. Detailed procedures for producing such deficient recombinant viruses for their replication may be found in applications WO 95/14785, WO 96/22378, U.S. Pat. No. 5,882,887, U.S. Pat. No. 6,013,516, U.S. Pat. No. 4,861,719, U.S. Pat. No. 5,278,056 and WO 94/19478 for example.

Another object of the present invention relates to a cell which has been transfected, infected or transformed with a nucleic acid and/or a vector according to the invention.

The term of "transformation" means the introduction of a gene or a "foreign" (i.e. extrinsic or extracellular) RNA or DNA sequence in a host cell, so that the host cell will express the gene or the introduced sequence for producing the substance of interest, typically a protein coded by the gene or the introduced sequence. A host cell which receives and expresses the introduced DNA or RNA has been "transformed".

The nucleic acids according to the invention may be used for producing a nanobody according to the invention in a suitable expression system. The term of "expression system" means a host cell and a compatible vector under suitable conditions, e.g. for the expression of a protein coded by the foreign DNA borne by the vector and introduced into the host cell.

Conventional expression systems include *Escherichia coli* host cells and plasmid vectors, insect host cells and Baculovirus vectors, and mammal host cells and their vectors. Other examples of host cells include prokaryotic cells (such as bacteria), and eukaryotic cells (such as yeast cells, mammal cells, insect cells, plant cells, etc.). Specific examples include *Escherichia coli*, *Kluyveromyces* or *Saccharomyces yeasts*, mammal cell lines (e.g. Vero cells, CHO cells, 3T3 cells, COS cells, etc.) as well as cell cultures of primary mammals or established cultures (e.g. produced from lymphoblasts, fibroblasts, epithelial cells, nerve cells, adipocytes, etc.). Examples also include SP2/0-Ag14 cells of mice (ATCC CRL1581), P3X63-Ag8.653 cells of mice (ATCC CRL1580), CHO cells in which a gene of dihydrofolate reductase is faulty, the YB2/3HL.P2.G11.16Ag.20 cells of rats (ATCC CRL1662), etc.

The present invention also relates to a method for producing a recombinant host cell expressing a nanobody according to the invention, said method comprising the steps consisting of: (i) introducing in vitro or ex vivo a nucleic acid or a recombinant vector as described above into a competent host cell, (ii) cultivating in vitro or ex vivo the obtained recombinant host cell and (iii) optionally selecting cells which express and/or secrete said nanobody. Such recombinant host cells may be used for producing nanobodies according to the invention.

The nanobodies according to the invention may be produced by any technique known to one skilled in the art, such as for example any chemical, biological, genetic or enzymatic technique, either alone or as a combination.

In particular, the invention further relates to a method for producing a nanobody according to invention, said method comprising the steps consisting of: (i) cultivating a transformed host cell according to the invention under suitable conditions for allowing expression of said nanobody, and (ii) recovering the expressed nanobody.

The nanobodies according to the invention may be suitably separated from the culture medium by conventional procedures for purifying immunoglobulins, such as for example A-Sepharose protein, hydroxyapatite chromatography, electrophoresis on a gel, dialysis or affinity chromatography.

Labelled Nanobodies

The nanobodies according to the invention are particularly useful for medical imaging. In this context, it is particularly of interest to have nanobodies associated with a detectable marker. The present inventors have shown that the nanobodies cAbVCAM1-5, cAbVCAM1-3, cAbVCAM1-8 and cAbVCAM1-9 retained their properties when they were associated with a detectable marker, in particular a radionuclide such as technetium 99 m.

The present invention therefore also relates to a nanobody as defined above associated with a detectable marker.

By "nanobody associated with a detectable marker", is meant here that the detectable marker is indirectly or directly bound to the nanobody, or is incorporated into the nanobody. The detectable marker may in particular be bound to the nanobody by substitution (for example, by substituting an H with an I at the tyrosine residues), by complexification or chelation.

By "detectable marker", is meant here a compound which produces a detectable signal. When it is associated with a tracer, it gives the possibility of following the outcome of the tracer in the organism. The detectable marker may be a MRI contrast agent, a scintigraphy contrast agent, an x-ray imaging contrast agent, an ultrasonic contrast agent, an optical imaging contrast agent. Examples of detectable markers include radionuclides, fluorophores, such as fluorescein, Alexa, cyanine; chemiluminescent compounds such as luminol; bioluminescent compounds such as luciferase or alkaline phosphatase; and contrast agents such as nanoparticles or gadolinium. The selection of the suitable detectable marker, which depends on the detection system used, is within the reach of one skilled in the art. As an example, when the detection system is MRI, the detectable marker is preferably a nanoparticle of iron oxide or of gadolinium; when the detection system is imaging by fluorescence, the detectable marker is preferably fluorescein, Alexa or cyanine; when the detection system is imaging by chemiluminescence, the detectable marker is preferably luminol; when the detection system is imaging by bioluminescence, the detectable marker is preferably luciferase or alkaline phosphatase; when the detection system is nuclear imaging, the detectable marker is preferably a radionuclide such as fluorine 18 ($^{18}F$) for TEP imaging, or technetium 99 m ($^{99m}Tc$) for SPECT imaging.

Preferably, the detectable marker is a radionuclide. Examples of radionuclides, which are more particularly used in nuclear imaging techniques, include technetium 99 m ($^{99m}$Tc), iodine 123 ($^{123}$I), iodine 125 ($^{125}$I), indium 111 ($^{111}$In), fluorine 18 ($^{18}$F), gallium 67 ($^{67}$Ga), gallium 68 ($^{68}$Ga), copper 64 ($^{64}$Cu) and any other radionuclide which may be used in humans. Therefore, preferably, the radionuclide is selected from the group consisting of $^{99m}$TC, $^{123}$I, $^{125}$I, $^{111}$In, $^{18}$F, $^{64}$Cu, $^{67}$Ga and $^{68}$Ga. Preferably, above all, the radionuclide is $^{99m}$Tc.

Use as a Contrast Agent

The inventors have demonstrated that the nanobodies cAbVCAM1-5, cAbVCAM1-3, cAbVCAM1-8 and cAbVCAM1-9 formed specific tracers of the atheroma plaque, in particular of the aortic plaque, and allow its detection by imaging.

The invention therefore proposes a nanobody as defined above for its use as a contrast agent in medical imaging, in particular non-invasive medical imaging in vivo.

It also relates to the use of a nanobody as defined above for manufacturing a contrast agent useful for medical imaging, in particular non-invasive medical imaging in vivo.

By "contrast agent", is meant here a substance or a composition which, administered into the organism, gives the possibility of marking in a detectable way organs or structures (tissue, cell, receptor) which, without any contrast agent, are not or not very visible in medical imaging. By extension, the expression "contrast agent" is used for designating a tracer associated with a marker as defined above.

Within the context of the invention, the "imaging methods" refer to methods which give the possibility of viewing the inside of an organism or organs of an organism. Examples of imaging methods include invasive techniques such as endocoronary echography, and non-invasive techniques such as magnetic resonance imaging, x-ray imaging, echography, optical imaging, or nuclear medicine such as scintigraphy, in particular one-photon emission tomography (SPECT) and positron emission tomography (PET). Preferably, the imaging method according to the invention is scintigraphy, in particular SPECT or PET scintigraphy.

Scintigraphy is based on the administration (generally via an intravenous route) of a contrast agent, also called a radio-pharmaceutical agent, consisting of a tracer marked with a radionuclide. Specific localisation of this contrast agent in the organism is then determined by detecting emitted gamma or beta rays.

One-photon emission tomography and positron emission tomography are tomographic nuclear medicine imaging techniques based on scintigraphy and which give the possibility of producing images and reconstructions in three dimensions of organs and of their metabolism by means of a set of cameras which rotate around the patient.

The present invention also relates to a medical imaging method, in particular a non-invasive medical imaging in vivo, in which a nanobody as defined above is administered to a patient. The medical imaging method according to the invention may further comprise steps for detecting the bond or the absence of a bond of the nanobody in body areas of the patient and steps for viewing the body areas of the patient in which the bond of the nanobody may be detected.

Within the context of the invention, a "patient" designates a human or non-human mammal, such as a rodent (rat, mouse, rabbit), a primate (chimpanzee), a feline (cat), a canine (dog). Preferably the individual is human.

Any administration method, known to one skilled in the art, may be used for administrating the nanobody according to the invention to the patient. In particular, the nanobody may be for example administered orally, by inhalation or via a parenteral route (in particular by intravenous injection). When the parenteral route is selected, the nanobody may be in the form of injectable solutions and suspensions, packaged in ampoules or flasks. The parenteral administration forms are conventionally obtained by mixing the nanobody according to the invention with buffers, stabilizers, preservatives, solubilizing agents, isotonic agents and suspending agents. According to known techniques, these mixtures may be sterilized or packaged as intravenous injections. One skilled in the art may for example use a buffer based on phosphate salts as buffers. Examples of suspension agents include methylcellulose, acacia, and sodium carboxymethylcellulose. Examples of stabilizers include sodium sulfite and sodium metasulfite, and examples of preservatives include sodium p-hydroxybenzoate, sorbic acid, cresol and chlorocresol.

The administered amount of nanobodies naturally depends on the administration route, on the size and/or on the weight of the patient, and on the detection technique used.

Within the context of the invention, the term of "body area" refers to a determined region of the organism. This may for example be an organ, a portion of an organ or a tissue, such as a lung, the heart, the liver, the spleen or a kidney, or a blood vessel such as an artery or a vein, in particular the aorta or the coronary arteries.

In a particular embodiment, the nanobody according to the invention is used as a contrast agent in medical imaging for viewing atherosclerotic plaques, more particularly aortic, carotidian or coronary atherosclerotic plaques, in a patient.

Within the context of the invention, the terms of "atherosclerotic plaque", "atherosclerosis plaque" and "atheroma plaque" are used indifferently and refer to a lesion of the walls of the vessels. Preferably, an atherosclerotic plaque comprises a lipid core and a fibrous cap, a cap consisting of smooth muscle cells, collagens and an extracellular matrix and isolating the lipid core from the arterial lumen. The atherosclerotic plaques may for example be found in the aorta, the carotid or in the coronary artery. When the plaque comprises a thin fibrous cap (with a thickness of about 65 to 150 µm) and a large lipid core, it is called a "vulnerable plaque" or "unstable plaque". These unstable plaques, which tend to disrupt, are encountered at the coronary arteries and at the aorta and its branches. The disruption of vulnerable coronary plaques causes "acute coronary syndromes". In the case of a complete occlusive thrombosis, this is myocardial infarction. When the thrombosis of the artery remains incomplete, this is unstable angina. At the carotid, the vulnerable plaques are more stenotic and less inflammatory. They also express VCAM-1.

Preferably, the nanobody according to the invention is used as a contrast agent in medical imaging for viewing vulnerable atherosclerotic plaques, in particular aortic or coronary vulnerable plaques.

Diagnostic Use

The appearance of atheroma plaques is a mark of atherosclerosis, which per se is a cardiovascular disease and may generate various cardiovascular complications. The detection of atheroma plaques therefore is the characterization of a cardiovascular disease. On the other hand, the possibility of following development by imaging, i.e. the progression or the regression of an atheroma plaque identified beforehand represents a method for evaluating the efficiency of a therapeutic treatment in a patient in which a cardiovascular disease was diagnosed.

The invention therefore relates to a nanobody as defined above for its use in diagnostic and prognostic methods.

By "diagnostic method" or "diagnosis", is meant here a method giving the possibility of determining whether an individual suffers from a pathology.

By "prognostic method" or "prognosis", is meant here a method giving the possibility of determining whether an individual risks developing a pathology.

Preferably, the nanobody as defined above is used for diagnosis of cardiovascular diseases.

Within the context of the present invention, by "cardiovascular disease", one designates a disease, a lesion or a symptom related to an atherogenesis process affecting the cardiovascular system. This notably includes the conditions marking development of an atheroma plaque (the plaques are classified in progression stages I to VI, according to the international Stary classification), as well as the complications resulting from the formation of an atheroma plaque (stenosis, ischemia) and/or its development towards an acute ischemic event (thrombosis, embolism, infarction, arterial disruption). Cardiovascular diseases for example designate atherosclerosis, an atheroma plaque, in particular the vulnerable plaque, the coronary disease, angina, thrombosis, cerebral vascular event, myocardial infarction, vascular stenosis, infarction. Preferably, the nanobody according to the invention is used for diagnosing atherosclerosis or a coronary disease.

By "atherosclerosis", is meant here a disease affecting arterial blood vessels. Atherosclerosis may be characterized by a chronic inflammatory response at the walls of the arteries, mainly due to the accumulation of macrophages and promoted by low density lipoproteins.

The "coronary disease" is the most current sign of the cardiovascular disease. It is a progressive disease, due to poor irrigation of the cardiac muscle, consecutive to shrinking (stenosis) or calcification (sclerosis) of the coronary artery or arteries. The main symptom of the coronary disease expresses itself as pains which make up an angina (either stable or unstable), also called angina pectoris. Complete obstruction of the coronary artery or arteries leads to infarction.

"Infarction" designates a circumscribed centre of necrosis due to arterial obstruction. More specifically, myocardial infarction is a necrosis of the myocardium which generally results from acute coronary thrombosis, secondary to a plaque disruption (generally a vulnerable plaque) causing platelet aggregation and then coronary occlusion.

The presence of a coronary atheroma plaque, especially if this is an unstable plaque, exposes the subject to a risk of acute ischemic stroke, notably myocardial infarction. The nanobody according to the invention may therefore be used for detecting a risk of occurrence of an acute ischemic stroke, in particular a risk of occurrence of myocardial infarction in a patient.

By "risk of occurrence", is meant here, the probability that an individual develops a pathology.

"Acute ischemic stroke" designates the decrease in the arterial blood provision in a territory of the organism. Its main local causes are thrombosis and embolism.

"Thrombosis" corresponds to blood coagulation in the vascular cavities (arteries, veins, capillaries or cardiac cavities) leading to the formation of a thrombus.

"Embolism" is the migration of a foreign body, most often consisting of a blood clot (thrombus), and its sudden stop in a vessel of which the caliber is insufficient for letting it through. The local consequences of embolism are circulatory perturbations related to vascular obstruction, most often leading to infarction.

The atheroma plaque may also be localized at a carotid artery. These lesions lead to a cerebral aemorrhagic (aneurysmal rupture) or ischemic (cerebral infarction) vascular event. The nanobody according to the invention may therefore be used for detecting a risk of occurrence of a cerebral vascular stroke in a patient.

This may still be an atheroma plaque localized at a renal artery, the kidney being one of the target organs of atherosclerosis. Significant stenosis may lead to arterial hypertension and/or kidney failure. Atheromatous affection of renal arteries may also lead to an acute vascular event, a renal embolism. The nanobody according to the invention may therefore be also used for detecting a risk of occurrence of a renal embolism in a patient.

The atheroma plaques may be localized at the arteries of lower limbs (acute ischemia risk of a limb), or at the aorta (risk of aneurysmal rupture/aortic dissection). The nanobody according to the invention may therefore be used for detecting a risk of occurrence of ischemia of a limb or of aortic aneurysmal rupture in a patient.

Therefore, the nanobody as defined above is preferably for a use in order to detect the risk of occurrence of an acute ischemic event selected from the group consisting of myocardial infarction, cerebrovascular stroke, renal arterial embolism and acute ischemic event of a limb.

The present invention also relates to a method, in particular a method in vitro for diagnosing a cardiovascular disease and/or detecting a risk of occurrence of an acute ischemic event in a patient, said method comprising steps consisting of administering a nanobody as defined above to said patient and of detecting said nanobody in the organism of said patient, the detection of a preferential localization of said nanobody at the cardiovascular system being an indicator of a cardiovascular disease and/or of a risk of occurrence of an acute ischemic event.

By "preferential localization", is meant that the detected amount of nanobody at the cardiovascular system is greater than the background noise which corresponds to non-specific localization of a nanobody in the organism.

The invention also relates to the nanobody as defined above for its use in therapeutic monitoring of a cardiovascular disease in a subject in whom a cardiovascular disease was diagnosed.

It also relates to the use of a nanobody as defined above for manufacturing a contrast agent useful for therapeutic follow-up of a cardiovascular disease in a subject in whom a cardiovascular disease was diagnosed.

By "therapeutic follow-up" is meant here, the observation of the response of the subject to the treatment which is administered to him/her. The therapeutic effect of a treatment is generally associated with a slowing down or an inhibition of the progression of a disease, with a reversion of the disease, or of one or several symptoms associated with this disease. Conversely, an absence of any therapeutic effect may be expressed by stability, or even acceleration of the progress of the disease or of one or several of its symptoms.

For example, if the cardiovascular disease in the sense of the invention is an atheroma plaque, the therapeutic follow-up may be carried out by observing the disappearance, the regression, the maintaining, or the growth of the atheroma plaque. Thus, the use according to the invention may comprise the steps consisting of:

a) administering a nanobody as defined above to a subject in whom an atheroma plaque was detected;
b) detecting the bond with the nanobody at said atheroma plaque;
c) repeating steps a) and b) before and after administering a treatment to said subject;

an absence or reduction of the bond of the nanobody at said plaque being an indicator of a treatment having a therapeutic effect.

Use as a Drug

The invention further relates to the use of a nanobody as defined above for manufacturing a drug, in particular a drug intended for treating a cardiovascular disease. A treatment method comprising the administration of a therapeutically effective amount of the nanobody as defined above to a patient in need thereof, is also part of the present invention.

The use of a VCAM-1 ligand alone or coupled with a stabilizer of the atheroma plaques, actually allows a reduction in the probability of disruption of the plaques.

By "treatment" of a cardiovascular disease, is meant "therapeutic treatment" (or curative treatment) of a cardiovascular disease, which includes slowing down or inhibiting the development of an atherosclerosis plaque, in particular to a stage of vulnerable atherosclerosis plaque, or regression of an atherosclerosis plaque, in particular of a vulnerable plaque. Also meant is the "prophylactic treatment" of a cardiovascular disease which notably includes the prevention of an acute ischemic stroke.

The nanobody according to the invention is advantageously coupled with a stabilizer of atheroma plaques, so as to put the stabilizer in contact with the lesion. The selection of a suitable stabilizer is within the reach of one skilled in the art. Examples of stabilizers notably include anti-inflammatory molecules such as non-steroidal anti-inflammatory agents.

The invention is more particularly related to the nanobody as defined above for its use for the treatment of atherosclerosis and/or preventing an acute ischemic stroke, preferably for treating a vulnerable atherosclerotic plaque.

The invention also relates to the use of a nanobody as defined above for manufacturing a drug intended for treating atherosclerosis and/or preventing an acute ischemic stroke in a patient who may have a cardiovascular disease.

The invention also relates to a method for treating atherosclerosis and/or preventing an acute ischemic stroke in a patient in need thereof, comprising the administration of a therapeutically effective amount of a nanobody as defined above to a patient in need thereof.

Preferentially, the nanobody according to the invention is used for treating a vulnerable atheroma plaque, still preferably a vulnerable coronary or aortic atheroma plaque.

Preferentially, said acute ischemic stroke is selected from the group consisting of myocardial infarction, cerebral vascular stroke, renal embolism, acute ischemia of a limb, and an aortic aneurysmal rupture.

The nanobody according to the invention may for example be administered orally, via inhalation, via a parenteral route (for example by intravenous injection), in a suitable form. When the parenteral route is contemplated, the nanobody may be in the form of injectable solutes and suspensions packaged in ampoules or flasks. The forms for parenteral administration are conventionally obtained by mixing the nanobody with buffers, stabilizers, preservatives, solubilizing agents, isotonic agents and suspension agents. According to known techniques, these mixtures are then sterilized and then packaged in the form of intravenous injections. As a buffer, one skilled in the art may use buffers based on organic phosphate salts, examples of suspension agents encompass methylcellulose, hydroxyethylcellulose, hydroxy-propylcellulose, acacia and sodium carboxymethylcellulose. Further, useful stabilizers according to the invention are sodium sulfite and sodium metasulfite, while mention may be made of sodium p-hydroxybenzoate, sorbic acid, cresol and chlorocresol as preservatives.

The administered amount of nanobody naturally depends on the administration method, on the size and/or on the weight of the patient, and on the nature of the cytotoxic agent which may be associated therewith.

The present invention also relates to a pharmaceutical composition comprising a nanobody as defined above in association with a pharmaceutically acceptable carrier.

The term "pharmaceutically" or "pharmaceutically acceptable" refers to molecular entities and compositions which do not produce secondary, allergic or other unfortunate reactions when they are administered to a mammal, in particular a human.

Within the context of the invention, the expression "pharmaceutically acceptable carrier" includes any solvent, dispersion medium, coating, antibacterial or antifungal agent, isotonic agent or absorption retardant, and the like. The use of such media and agents for the pharmaceutically active substances is well known to one skilled in the art. Except for the case when a conventional medium or agent is incompatible with the active ingredient, its use is contemplated in pharmaceutical compositions. Additional active ingredients may also be incorporated into the composition.

Use for Detecting VCAM-1 In Vitro

The present invention also relates to the use of a nanobody as defined above for in vitro detection of VCAM-1 in a sample.

By "sample", is meant here a portion of a larger element. Preferably, the sample is a substance of biological origin. Examples of biological samples include, but are not limited thereto, portions of organs or tissues such as the kidney, the liver, heart, the lung, etc., the arteries, the veins, etc., the blood and its compounds such as the plasma, the platelets, the sub-populations of blood cells etc.

EXAMPLE

The example below shows the specific properties of the nanobodies cAbVCAM1-5, cAbVCAM1-3, cAbVCAM1-8 and cAbVCAM1-9 according to invention as compared with other anti-VCAM-1 nanobodies.

Equipment and Methods
Generation and Production of Nanobodies

Nanobodies targeting VCAM-1 were generally generated according to methods published earlier (Arbabi Ghahroudi et al. (1997) *FEBS Lett.* 414:521-526). More specifically, a dromedary was immunized with both human and murine recombinant VCAM-1 proteins (RnD Systems, Minneapolis, USA). The blood lymphocytes were isolated and the RNA was purified. The variable domains of the single chain antibodies (VHH or nanobodies) were amplified by using the two-step RT-PCR technique and cloned in phase with the protein 3 of the bacteriophage M13. The nanobodies were subject to phage-display and used in biopanning on immobilized immunogens. Total bacterial extracts containing soluble nanobodies were used for selecting individual VCAM-1 ligands on the basis of a positive signal in ELISA and in flow cytometry on bEND5 cells stimulated with TNFα. After sequencing, the selected anti-VCAM-1 nanobodies and the irrelevant control nanobodies cAbBcII10 were produced as tagged proteins with hexahistidine in *E. coli* and purified as described in Saerens et al. (2005) *J. Mol. Biol.* 352:597-607.

In Vitro Evaluation of Non-Labelled Nanobodies

Cell Line—

The endothelial cell line of bEND5 mice (ECACC, Salisburg, GB) was cultivated in a supplemented DMEM lesion. The expression of VCAM-1 was induced by stimulation with 10 ng/mL of TNFα for 18 hours.

Flow Cytometry—

$10^5$ bEND5 cells stimulated with TNFα and non-stimulated were incubated with either 200 ng of mouse anti-VCAM-1 monoclonal antibodies marked with PE (mAb; Abcam), or sequentially with 1 μg of nanobodies, 1 μg of anti-His-tag monoclonal antibodies (Serotec) and 200 ng of anti-mouse rat $IgG_1$ (BD Biosciences). The bond was measured on a FACS Canto II analyzer (BD Biosciences, Franklin Lakes, USA) and the data analyzed with the FlowJo software package (TreeStar, Ashland, USA).

Thermal Stability—

The values of $T_m$ (unfolding temperatures) were obtained on a spectropolarimeter J-715 (Jasco, Easton, Md., USA) as described in Vaneycken et al. (2010) *J. Nucl. Med.* 51:1099-1106.

Evaluation of the Affinity Based on Surface Plasmon Resonance (SPR)—

The affinity of human or murine recombinant VCAM-1 nanobodies was determined by SPR analysis on a Biacore™ 3000 apparatus. Recombinant mouse ICAM-1 (R&D Systems) was used as a negative control. The recombinant proteins were immobilized on a sensor chip CM5 (Biacore™, Uppsala, Sweden) according to the instructions of manufacturer. Serial half-dilutions of the nanodbodies from 50 to 1 nM in PBS with 0.005% Tween-20® were tested. The affinity constants were determined by using adjustment of the standard association model 1:1 (BIAevaluation software package).

Competition with the Epitope by Using SPR—

SPR was used for determining which nanobodies were competing for the same epitope. The procedures used are identical with those described in Vaneycken et al. (2011) *FASEB J.* 25:2433-2446.

Radiolabeling and Determining of the Stability In Vitro and In Vivo by HPLC

The nanobdodies were radiolabeled with $^{99m}$Tc by using the tricarbonyl method as described in Gainkam et al. (2008) *J. Nucl. Med.* 49:788-795. The radiochemical purity was immediately evaluated after the labeling, after 6 hours at 20° C. in PBS and in mouse blood 3 hours after injection (p.i.). In the latter case 100 μL of sampled total blood were centrifuged and the plasma was filtered by using a Nanosep 10K Omega membrane. The radiochemical purity was determined by RP-HPLC by using a column C4 eluted with a mobile phase in an ACN/TFA gradient. The radioactivity was viewed by using a radiodetector (γ-RAM Model 4, LabLogic).

Evaluation In Vitro of the Nanobodies Marked with $^{99m}$Tc $250 \times 10^3$ bEND5 cells were sown in 24-well plaques and stimulated for 18 hours with TNFα at 10 ng/mL. 5 nM of each nanobody—$^{99m}$Tc were incubated in 0.5 mL of PBS+ 1% of human albumen serum (HSA) for 1.5 hours at 37° C. Competition studies with an excess of 500 times the non-labelled nanobody, were conducted in order to determine the bond specificity. After washing, the bound $^{99m}$Tc-nanobodies were collected and counted in a gamma counter (Cobra II Inspector 5003, Canberra Packard, USA). The experiments were conducted in triplicate. The non-specific bond to the wells was subtracted, and the results were normalized to the TNFα-negative condition.

Animal Model and Treatment of the Aortas

All the animal experiments were approved by the committee from the "Recherche du Service de Santé des Armées de Grenoble (CRSSA)", (Research Centre of the Army Health Services of Grenoble). Female control mice and ApoE$^{-/-}$ mice of 31±1 weeks of age were used (Charles-River, France). The ApoE$^{-/-}$ mice (n=37) were fed with a Western diet containing 0.39% of cholesterol (Safe, France), while the C57Bl/6J control mice (n=9) were fed with a standard food diet. Each anti-VCAM-1 nanobody was evaluated on 3 ApoE$^{-/-}$ mice except the nanobody cAbVCAM1-5 (n=6), which was further evaluated on C57Bl/6J control mice (n=4). The antibody cAbBcII10 was evaluated as a negative control both in the ApoE$^{-/-}$ mice (n=4) and the control mice (n=5). Two hours after administration of nanobodies radiolabeled with $^{99m}$Tc (67±4 MBq i.v.), the mice were anesthetised by using 2% Isoflurane (Baxter) and SPECT/CT acquisition was carried out (nanoSPECT, Bioscan, see below). The mice were euthanized by an overdose of sodium pentobarbital (CEVA) and the aortas, as well as the other major organs were carefully recovered. The aortas were separated from the adherent tissues in a solution of formalin at 10% and cut into 12 segments from the ascending aorta as far as the iliac bifurcation. An extension index of the lesion was assigned to each segment as follows: (−) no lesion (control segments), (+) lesions covering up to 50% of the length of the arterial segment, (++) lesions covering more than 50% of the length of the arterial segment and (+++) lesions extending over the whole length of the segment. The aortic segments and the tissue samples were weighed and their activity was determined by a well gamma counter (Cobra II, Packard). The results were corrected as regards background noise and radioactive decay and expressed as a percentage of the injected dose per gram of tissue (% ID/g). The absorptions of the aortic lesions and of the control were defined as the average absorption in all the segments classified as (+++) or (−) respectively. The lesion-to-control, lesion-to-blood and lesion-to-heart ratios were also determined.

Adjacent cryo-sections with a thickness of 20 and 8 μm were obtained from 12 aortic segments obtained by imaging with micro-autoradiography (BASS-5000, Fujifilm) and immunohistological marking of VCAM1, respectively.

Further, blood clearance of $^{99m}$TC-cAbVCAM1-5 was evaluated in 3 C57Bl/6 mice by recovering blood samples at different times after injection. The results were expressed in % ID in the total blood volume (% ID/TBV).

Immunohistochemistry

After 1 hour of blocking at 20° C. with 10% of donkey serum, an anti-VCAM-1 goat primary antibody (Santa-Cruz Biotechnology, 0.5 μg/ml) was applied on the aortic sections overnight at 4° C. An anti-goat donkey biotinylated secondary antibody (Jackson ImmunoResearch) was incubated for 1 hour at 20° C. and the DAB was used as a color forming agent. The sections were counter-colored with hematoxylin. The marking specificity was checked by omitting the primary antibody on control slides. In a sub-group of control mice and ApoE$^{-/-}$ mice, VCAM-1 immuno-marking was carried out on the heart, the muscle, the salivary glands, the bone marrow, the lymphatic ganglions, the spleen and the thymus.

SPECT/CT Imaging

Two hours before the intravenous injections, the anesthetized animals were placed in a bed with a controlled temperature and entire body SPECT/CT acquisitions were carried out (nanoSPECT, Bioscan). The approximate CT acquisition time was 10 mins, by using the following acquisition parameters: 45 kVp, 240 projections and 1,000 ms per projection. Helical SPECT acquisition was carried out with 4 heads equipped with stenopeic multiple hole collimators with a resolution of 1 mm (9×1.4 mm of whole diameter per head) by using 24 projections and 45 minutes of acquisition. The CT and SPECT acquisitions were reconstructed, merged and quantified by using the dedicated software package (InVivoScope). The regions of interest (ROIs) were drawn at the aortic arch, at the left ventricle cavity and at the left ventricle wall in order to determine the arch-to-blood and arch-to-heart ratios.

Autoradiography

For each animal, autoradiographic images were obtained after one night of exposure of 3 groups of slides with a thickness of 20 μm obtained at different levels of the 12 aortic segments. The images were quantified by using the dedicated software package (IMAGE GAUGER, Fujifilm). The ROIs were drawn around atherosclerotic lesions and the negative control VCAM-1 aortic wall. The results were corrected for the background noise and expressed in the form of average lesion-to-control ratios.

Evaluation of the Reactivity of Non-Radio-Labelled Nanobodies Against Rabbit VCAM-1

$10^5$ CHO cells either transiently transfected or not with a plasmid coding for rabbit VCAM-1 were sequentially incubated with 1 μg of nanobodies, 1 μg of anti-His-tag monoclonal antibody (Serotec) and 200 ng of anti-mouse rat IgG$_1$ (BD Biosciences). The bond was measured on a FACS Canto II analyzer (BD Biosciences, Franklin Lakes, USA) and the data analysed with the FlowJo™ software package (TreeStar, Ashland, USA). A negative control was made by omitting the nanobody.

Statistical Analysis

All the results were displayed in the form of a mean±standard error of the mean. Mann & Witney U and Wilcoxon non-parametric tests were used for comparing paired and non-paired data. The differences were considered as significant for $p<0.05$.

Results

Generation of the Anti-VCAM-1 Nanobodies

The inventors sought to develop cross-reaction nanobodies for human and murine VCAM-1. Therefore, the nanobodies were generated by immunizing a dromedary with both human and murine recombinant proteins VCAM-1 and by biopanning the library of immune nanobodies obtained by the phage display resulting therefrom. Total bacterial extracts containing the individual nanobodies were screened in ELISA for their bond with the VCAM-1 recombinant proteins and in flow cytometry for their bond to the bEND5 cells expressing VCAM-1.

After sequencing, 31 anti-VCAM-1 nanobodies were identified and grouped into 12 families on the basis of the similarity of the sequences in the loops for binding to the antigen. Six families of nanobodies were specific of murine VCAM-1 (mVCAM-1) and 6 families bound both to murine VCAM-1 and human VCAM-1 (hVCAM-1). On the basis of ELISA signals and of flow cytometry of the total extracts, 10 nanobodies (designated as cAbVCAM1-1 to -10) were selected for being analyzed in more detail. The nanobody production yield was from 0.5 to 10.5 mg/L of bacterial culture (Table 4).

Characterizations In Vitro

The flow cytometry experiments on bEND5 cells showed that the 12 selected nanobodies interacted with VCAM-1 (FIG. 1). As demonstrated by SPR analysis, summarized in Table 4, all the selected nanobodies bound to VCAM-1 with high affinities ranging from 0.2 to 45.7 nM. Further, from among the 10 selected nanobodies, 6 were cross-reactive with hVCAM-1 with affinities remaining of the order of 1 nanomolar (Table 4). These six nanobodies were cAbVCAM1-1, cAbVCAM1-3, cAbVCAM1-5, cAbVCAM1-8, cAbVCAM1-9 and cAbVCAM1-10. On the basis of SPR competition studies, the nanobodies cAbVCAM1 were grouped into 3 categories for epitope targeting: cAbVCAM1-1/5, cAbVCAM1-2/3/6/7/9/10 and cAbVCAM1-4/8. All the nanobodies showed strong thermal stability as demonstrated by the unfolding temperatures ranging from 59.4 to more than 87° C. (Table 4).

TABLE 4

Comparison between the 10 evaluated anti-VCAM-1 nanobodies.

| Radiotracer | % ID/g of lesion | Lesion/Control | Lesion/Blood | Lesion/Heart | $K_D$ mVCAM-1 (nM) | $K_D$ hVCAM-1 (nM) | Production Yield (mg/L) | $T_m$ (° C.) |
|---|---|---|---|---|---|---|---|---|
| cAbVCAM1-1 | 0.87 ± 0.08 #9 | 2.15 ± 0.20 #9 | 0.74 ± 0.10* #10 | 2.65 ± 0.23* #9 | 8.3 ± 1.2 #7 | 12.4 ± 0.5 #5 | 2.0 #7 | 72.3 ± 0.1 #2 |
| cAbVCAM1-2 | 2.15 ± 0.29* #6 | 2.90 ± 0.45 #2 | 3.37 ± 0.32* #5 | 5.55 ± 0.58* #7 | 0.3 ± 0.0 #2 | Non-cross reactive | 5.0 #5 | 62.3 ± 0.1 #6 |
| cAbVCAM1-3 | 2.95 ± 0.16* #2 | 4.07 ± 0.56 #3 | 5.06 ± 0.39* #1 | 7.40 ± 0.91* #3 | 2.4 ± 0.1 #5 | 9.1 ± 0.9 #4 | 6.8 #3 | 59.7 ± 0.1 #9 |
| cAbVCAM1-4 | 2.21 ± 0.59* #5 | 3.20 ± 0.74 #5 | 1.41 ± 0.29 #9 | 1.96 ± 0.56* #10 | 0.2 ± 0.0 #1 | Non-cross reactive | 6.8 #3 | 59.4 ± 0.1 #10 |
| cAbVCAM1-5 | 2.53 ± 0.08* #3 | 4.95 ± 0.85* #1 | 4.32 ± 0.48* #2 | 8.30 ± 1.11* #1 | 2.0 ± 0.0 #4 | 6.5 ± 0.7 #3 | 10.5 #1 | >87 #1 |
| cAbVCAM1-6 | 0.73 ± 0.08 #10 | 4.57 ± 0.93* #2 | 1.85 ± 0.37 #8 | 4.98 ± 0.75 #8 | 5.2 ± 0.6 #6 | Non-cross reactive | 3.0 #6 | 72.0 ± 0.1 #3 |
| cAbVCAM1-7 | 1.27 ± 0.25* #8 | 2.88 ± 0.65 #7 | 4.02 ± 1.05* #3 | 5.98 ± 0.96 #4 | 26.6 ± 1.2 #9 | Non-cross reactive | 6.9 #2 | 60.9 ± 0.3 #8 |
| cAbVCAM1-8 | 2.48 ± 0.46* #4 | 1.40 ± 0.10 #10 | 3.66 ± 0.10* #4 | 7.71 ± 0.38* #2 | 13..2 ± 0.3 #8 | 1.4 ± 0.5 #1 | 1.5 #8 | 61.5 ± 0.1 #7 |
| cAbVCAM1-9 | 2.99 ± 0.07* #1 | 2.19 ± 0.60 #8 | 2.51 ± 0.03* #6 | 5.69 ± 0.36* #6 | 0.9 ± 0.2 #3 | 5.3 ± 0.7 #2 | 0.9 #9 | 66.8 ± 0.2 #4 |

TABLE 4-continued

Comparison between the 10 evaluated anti-VCAM-1 nanobodies.

| Radiotracer | % ID/g of lesion | Lesion/Control | Lesion/Blood | Lesion/Heart | K$_D$ mVCAM-1 (nM) | K$_D$ hVCAM-1 (nM) | Production Yield (mg/L) | T$_m$ (° C.) |
|---|---|---|---|---|---|---|---|---|
| cAbVCAM1-10 | 1.93 ± 0.14* #7 | 3.47 ± 0.67* #4 | 2.01 ± 0.14* #7 | 5.76 ± 0.56* #5 | 45.7 ± 20.0 #10 | 18.4 ± 7.0 #6 | 0.8 #10 | 63.4 ± 0.2 #5 |
| cAbBcII10 | 0.68 ± 0.06 | 1.66 ± 0.28 | 1.57 ± 0.09 | 4.00 ± 0.14 | — | — | — | — |

The mean ± standard mean error and the rank #are given for the parameters obtained either ex vivo by well gamma counting (% ID/g of lesion, lesion-to-control ratio, lesion-to-blood ratio, lesion-to-heart ratio), or in vitro (K$_D$ for mVCAM-1 or hVCAM-1, production yield and T$_m$).
*p < 0.05 versus cAbBcII10.

Figure 2:
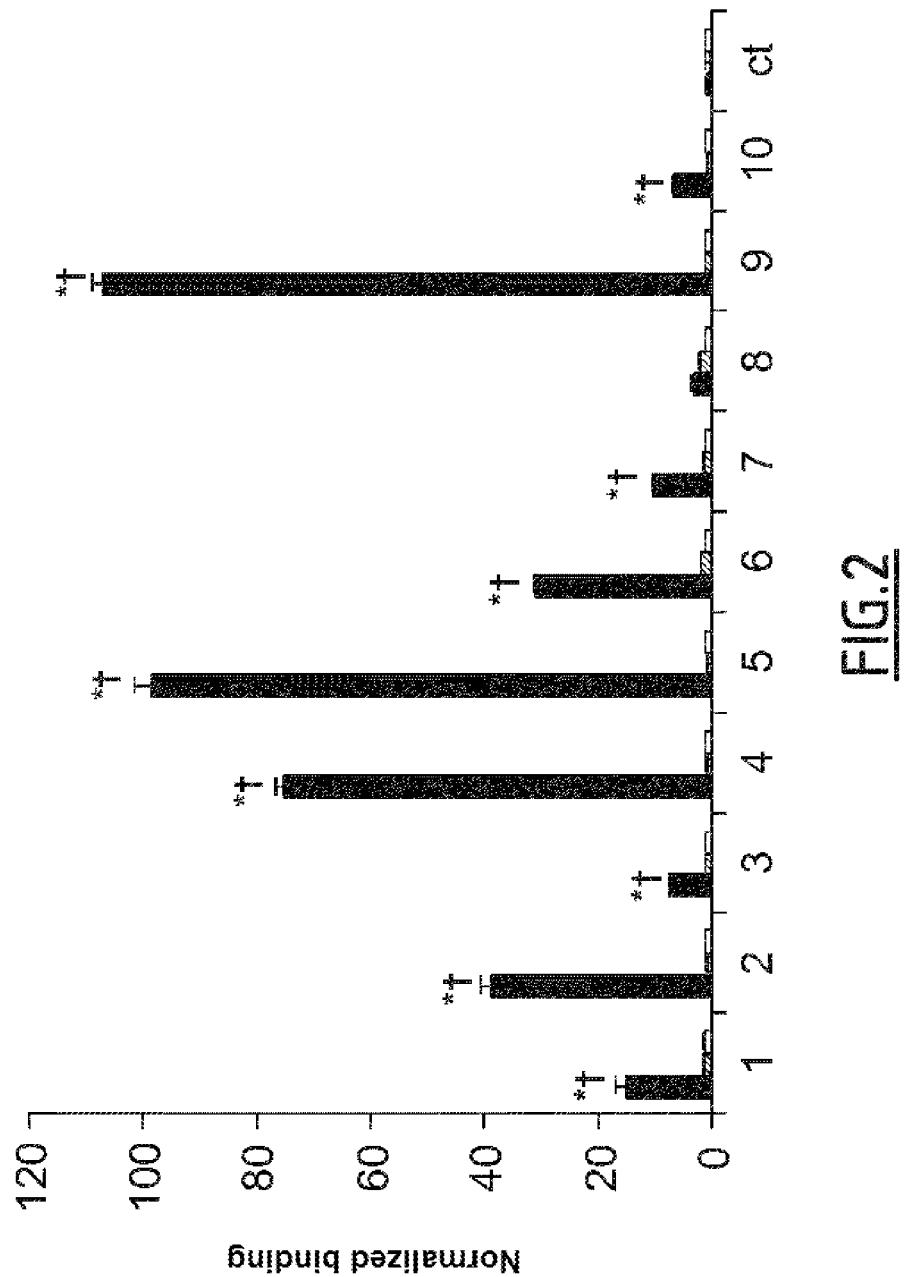
FIG. 2 illustrates histograms showing the normalized bond of the anti-VCAM-1 nanobodies (cAbVCAM1-1: 1; cAbVCAM1-2: 2; cAbVCAM1-3: 3; cAbVCAM1-4: 4; cAbVCAM1-5: 5; cAbVCAM1-6: 6; cAbVCAM1-7: 7; cAbVCAM1-8: 8; cAbVCAM1-9: 9 and cAbVCAM1-10: 10) marked with $^{99m}$Tc to untreated bEND5 cells (white bars), treated with TNFα (and therefore expressing VCAM-1; black bars) or treated with TNFα and incubated with an excess of anti-VCAM-1 nanobodies not marked (grey bars). *: $P<0.05$ versus $^{99m}$Tc-AbBcII10. †: $P<0.05$ versus treated with TNFα and incubated with an excess of non-marked anti-VCAM-1 nanobodies.

Subsequently to the radiolabeling steps with $^{99m}$Tc and of purification, the radiochemical purities were greater than 95% for the 10 nanobodies cAbVCAM1 and the control nanobody cAbBcII10. Labelling with $^{99m}$Tc is not affected by the recognition of VCAM-1 for most ligands, as demonstrated by the in vitro binding test on bEND5 cells (FIG. 2): the inventors actually showed that the bond to positive VCAM-1 endothelial cells, stimulated with TNFα, was significantly stronger than on the stimulated cells. Further, the binding to cells stimulated with TNFα was successfully inhibited by competition with an excess of non-marked nanobodies, which demonstrates their specificity.

Analyses of the Bio-Distributions

The bio-distributions of the nanobodies labelled with $^{99m}$Tc in ApoE$^{-/-}$ mice are summarized in Table 5. All the nanobodies including the control cAbBcII10, showed a strong absorption at the kidneys, ranging from 97±16 to 315±33% ID/g and strong activities in the bladder. Interestingly, the absorptions of $^{99m}$Tc-cAbVCAM1 were high in the lymphoid tissues and even reached a statistical difference for $^{99m}$Tc-cAbVCAM1-3 (spleen and thymus), $^{99m}$Tc-cAbVCAM1-4/5 (spleen, thymus and bone marrow) and $^{99m}$Tc-cAbVCAM1-9 (thymus) (p<0.05 versus $^{99m}$Tc-cAbBcII10). Except for the lungs and the liver (mean absorption of 2.5±0.8 and 2.7±0.9% ID/g, respectively), the absorption was less than 2% ID/g in the other studied tissues, including blood and the myocardium.

As shown in Table 4, the absorption in the atherosclerotic lesions was greater than 2% ID/g for 6 of the 10 nanobodies cAbVCAM1, with a maximum value of 2.99±0.14% ID/g for $^{99m}$Tc-cAbVCAM1-9 (P<0.05 versus $^{99m}$Tc-cAbBcII10).

The lesion-to-control, lesion-to-blood and lesion-to-heart ratios were determined from bio-distribution data (Table 4). The lesion-to-control ratio was greater than 2 for all the evaluated nanobodies cAbVCAM1 except one, with a maximum ratio of 4.95±0.85 for cAbVCAM1-5 (P<0.05 versus $^{99m}$Tc-cAbBcII10). The lesion-to-blood ratio was greater than 1 for all the evaluated nanobodies cAbVCAM1 except for one, with a maximum ratio of 5.6±0.39 for $^{99m}$Tc-cAbVCAM1-3 (P<0.05 versus $^{99m}$Tc-cAbBcII10). Finally, the lesion-to-heart ratio was greater than 1 for all the nanobodies with a maximum value of 8.30±1.11 for $^{99m}$TC-cAbVCAM1-5 (P<0.05 versus $^{99m}$Tc-cAbBcII10).

TABLE 5

Bio-distribution ex vivo of anti-VCAM-1 nanobodies labelled with $^{99m}$Tc, 3 hours after injection in hypercholesterolemic mice ApoE$^{-/-}$

| | ApoE$^{-/-}$ cAbVCAM1- | | | | | |
|---|---|---|---|---|---|---|
| | 1 | 2 | 3 | 4 | 5 | 6 |
| Blood | 1.2 ± 0.1* | 0.6 ± 0.1 | 0.6 ± 0.0 | 1.5 ± 0.1* | 0.6 ± 0.1 | 0.4 ± 0.1 |
| Heart | 0.3 ± 0.0 | 0.4 ± 0.1* | 0.4 ± 0.0* | 1.1 ± 0.0* | 0.3 ± 0.1* | 0.2 ± 0.0 |
| Lung | 3.2 ± 0.6 | 1.5 ± 0.2 | 3.2 ± 0.5 | 4.1 ± 1.0* | 2.3 ± 0.3* | 1.7 ± 1.1 |
| Liver | 2.2 ± 0.2* | 2.0 ± 0.1 | 1.5 ± 0.1 | 8.3 ± 0.7* | 1.8 ± 0.3* | 0.8 ± 0.1 |
| Skeletal muscle | 0.6 ± 0.4 | 0.1 ± 0.0 | 0.2 ± 0.0 | 0.2 ± 0.0 | 0.2 ± 0.0 | 0.2 ± 0.1 |
| Skin | 0.2 ± 0.1 | 0.3 ± 0.1 | 0.3 ± 0.0 | 0.9 ± 0.5 | 0.4 ± 0.0 | 0.3 ± 0.0 |
| Fat | 0.1 ± 0.0 | 0.1 ± 0.0 | 0.1 ± 0.0 | 0.2 ± 0.0 | 0.1 ± 0.0* | 0.1 ± 0.0 |
| Brain | 0.0 ± 0.0* | 0.1 ± 0.0* | 0.1 ± 0.0* | 0.2 ± 0.0 | 0.1 ± 0.0* | 0.0 ± 0.0 |
| Salivary glands | 0.9 ± 0.3* | 0.4 ± 0.0 | 0.5 ± 0.0 | 1.2 ± 0.1* | 0.5 ± 0.1* | 0.3 ± 0.0 |
| Pancreas | 0.3 ± 0.1 | 0.2 ± 0.0 | 0.3 ± 0.0 | 0.6 ± 0.0* | 0.3 ± 0.0* | 0.2 ± 0.0 |
| Thyroid | 0.9 ± 0.2 | 0.5 ± 0.2 | 1.0 ± 0.2 | 1.5 ± 0.2 | 0.7 ± 0.1 | 1.0 ± 0.6 |
| Stomach | 0.6 ± 0.0 | 0.6 ± 0.1 | 0.6 ± 0.0 | 1.5 ± 0.3* | 0.6 ± 0.1* | 0.3 ± 0.0 |
| Bile | 0.9 ± 0.2 | 0.4 ± 0.1 | 1.7 ± 1.0 | 0.5 ± 0.0 | 0.7 ± 0.2 | 0.5 ± 0.1 |
| Intestine | 1.4 ± 0.8 | 0.5 ± 0.1 | 0.5 ± 0.0 | 0.7 ± 0.4* | 0.5 ± 0.1* | 0.3 ± 0.1 |
| Kidney | 125 ± 13 | 228 ± 34 | 303 ± 68 | 97 ± 16* | 222 ± 12 | 207 ± 31 |
| Urine | 265 ± 84* | 59 ± 14 | 96 ± 35 | 58 ± 33 | 83 ± 15 | 77 ± 18 |
| Rate | 2.9 ± 0.2 | 8.0 ± 0.3 | 20.3 ± 11.4* | 35.7 ± 0.3* | 9.2 ± 1.0* | 1.7 ± 0.0 |
| Thymus | 0.4 ± 0.1 | 0.7 ± 0.1 | 1.9 ± 0.1* | 2.2 ± 0.6* | 1.7 ± 0.1* | 0.4 ± 0.0 |
| Bone marrow | 2.6 ± 0.3 | 5.9 ± 0.8 | 13.7 ± 5.6 | 31.8 ± 2.2* | 10.7 ± 2.9* | 1.9 ± 0.2 |

| | ApoE$^{-/-}$ cAbVCAM1- | | | | cAbBcII10 |
|---|---|---|---|---|---|
| | 7 | 8 | 9 | 10 | |
| Blood | 0.3 ± 0.0 | 0.6 ± 0.1 | 1.2 ± 0.0* | 1.0 ± 0.2* | 0.4 ± 0.0 |
| Heart | 0.2 ± 0.0 | 0.3 ± 0.1 | 0.5 ± 0.0* | 0.4 ± 0.1 | 0.2 ± 0.0 |

TABLE 5-continued

Bio-distribution ex vivo of anti-VCAM-1 nanobodies labelled with $^{99m}$Tc, 3 hours after injection in hypercholesterolemic mice ApoE$^{-/-}$

| | | | | | |
|---|---|---|---|---|---|
| Lung | 1.3 ± 0.2 | 2.1 ± 0.6 | 2.5 ± 0.1 | 2.07 ± 1.0 | 1.0 ± 0.2 |
| Liver | 1.2 ± 0.2 | 3.1 ± 0.3* | 2.4 ± 0.2* | 4.0 ± 0.4* | 0.7 ± 0.0 |
| Skeletal muscle | 0.1 ± 0.0 | 0.2 ± 0.1 | 0.2 ± 0.0 | 0.2 ± 0.0 | 0.1 ± 0.0 |
| Skin | 0.4 ± 0.0 | 0.6 ± 0.2 | 0.4 ± 0.1 | 0.4 ± 0.1 | 0.3 ± 0.0 |
| Fat | 0.1 ± 0.0 | 0.2 ± 0.1 | 0.1 ± 0.0 | 0.1 ± 0.0 | 0.1 ± 0.0 |
| Brain | 0.0 ± 0.0 | 0.0 ± 0.0 | 0.1 ± 0.0* | 0.0 ± 0.0* | 0.0 ± 0.0 |
| Salivary glands | 0.5 ± 0.1 | 0.6 ± 0.3 | 0.6 ± 0.1 | 0.7 ± 0.1 | 0.2 ± 0.0 |
| Pancreas | 0.2 ± 0.0 | 0.3 ± 0.1 | 0.4 ± 0.0* | 0.3 ± 0.1 | 0.1 ± 0.0 |
| Thyroid | 0.9 ± 0.2 | 1.1 ± 0.4 | 1.3 ± 0.5 | 1.4 ± 0.1 | 0.1 ± 0.0 |
| Stomach | 0.5 ± 0.1 | 0.7 ± 0.1 | 0.7 ± 0.0 | 0.7 ± 0.1 | 0.4 ± 0.1 |
| Bile | 0.9 ± 0.1 | 1.1 ± 0.1 | — | 0.8 ± 0.2 | 0.4 ± 0.1 |
| Intestine | 0.6 ± 0. | 0.5 ± 0.1 | 0.6 ± 0.0 | 0.5 ± 0.1 | 0.2 ± 0.1 |
| Kidney | 254 ± 18 | 315 ± 33 | 158 ± 6 | 304 ± 32 | 266 ± 14 |
| Urine | 92 ± 25 | 27 ± 7 | 98 ± 12 | 44 ± 14 | 41 ± 10 |
| Rate | 1.6 ± 0.1 | 1.6 ± 0.2 | 8.0 ± 1.2 | 4.3 ± 0.5 | 0.4 ± 0.0 |
| Thymus | 0.5 ± 0.0 | 0.5 ± 0.1 | 1.5 ± 0.2* | 0.3 ± 0.2 | 0.2 ± 0.0 |
| Bone marrow | 2.6 ± 0.1 | 1.5 ± 0.3 | 7.0 ± 0.8 | 3.2 ± 0.7 | 1.0 ± 0.7 |

The results are expressed in mean ± mean standard error.
*p < 0.05 versus cAbBcII10.

Immunohistochemistry

Figure 3:
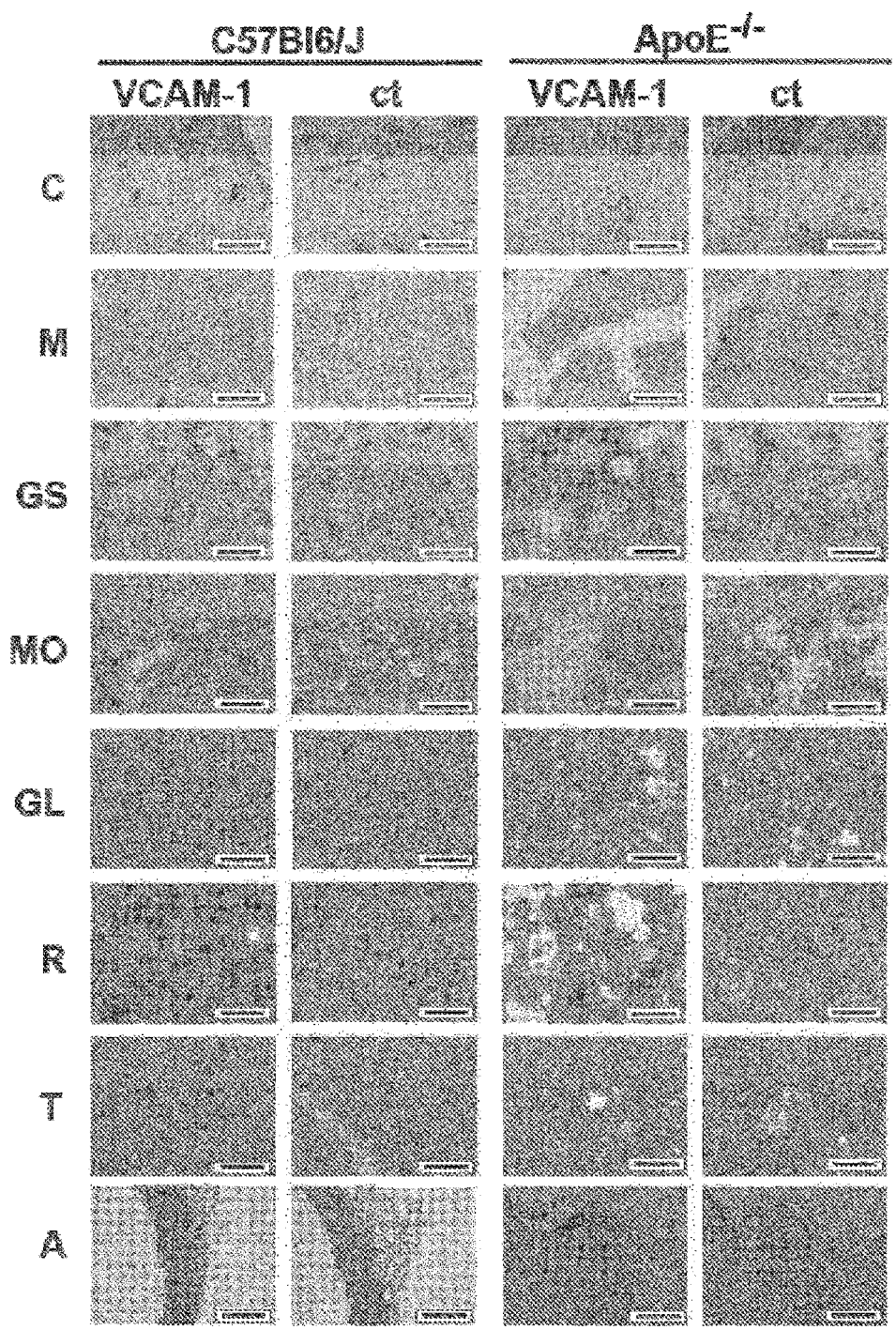
FIG. 3 shows the results of immunohistochemistry on heart (C), muscle (M), salivary gland (GS) samples, samples of lymphatic tissues including samples of bone marrow (MO), lymphatic ganglion (GL), spleen (R) and thymus (T), and aorta samples (A) of C57Bl/6J control mice and of ApoE$^{-/-}$ mice, marked with an anti-VCAM-1 nanobody (VCAM-1). The specificity of the results is shown by the absence of marking in the absence of any primary antibody (ct). The scale bar represents 20 µm, except for the aorta (A) where it represents 100 µm.

As shown in FIG. 3, a constitutive expression of VCAM-1 was observed in lymphoid tissues (i.e. bone marrow, lymphatic ganglions, spleen and thymus) both in control mice C57Bl/6J and hypercholesterolemic mice ApoE$^{-/-}$, while no expression of VCAM1 was found in the heart, the muscles and the salivary glands. Further, strong VCAM-1 marking was also observed in aortic lesions, at the endothelium, as well as inside the atherosclerotic plaque, but not in the aorta of the C57Bl/6J control mice.

Absorption of cAbVCAM1-5 in Atherosclerotic Lesions: Imaging Ex Vivo and In Vivo On the basis of the selection criteria summarized in Table 4, the nanobodies cAbVCAM1-5, cAbVCAM1-3, cAbVCAM1-8 and cAbVCAM1-9 were considered by the inventors as the most promising for being used as radiotracers in medical imaging. The nanobody cAbVCAM1-5 was more particularly selected to be the subject of additional evaluations.

Aortic Absorption—

Figure 4:
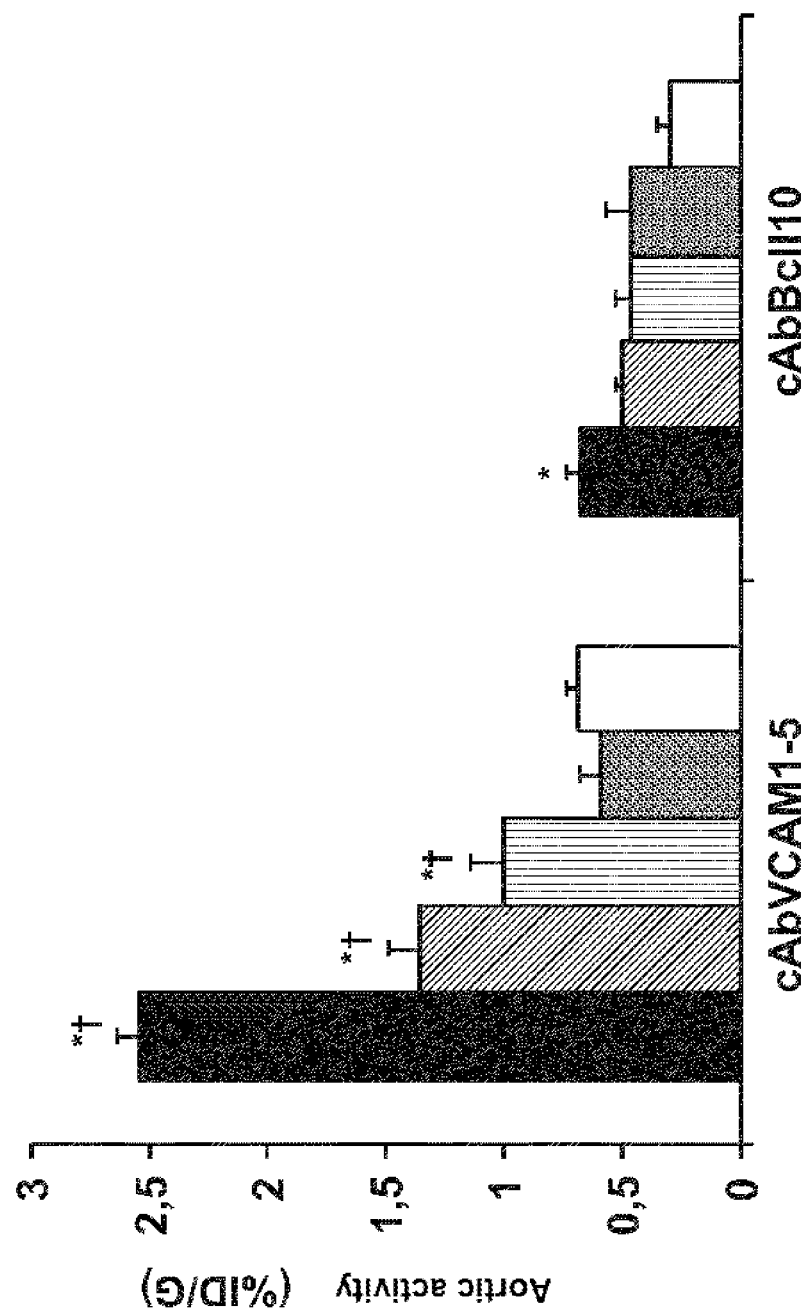
FIG. 4 illustrates histograms showing aortic absorption (in % ID/g) of the nanobody cAbVCAM1-5 and of the control nanobody cAbBcII10 in the aorta of C57Bl/6J control mice (white bars) and the ApoE$^{-/-}$ arterial segments ordered according to the extension index of the lesion (+++: black bars; ++: diagonal hatched bars; +: vertical hatched bars; −: dotted bars). The results are expressed in mean±standard error on the mean. *: $P<0.05$ versus C57Bl/6J. †: $P<0.05$ versus extension index of the next lesion.
Figure 5:
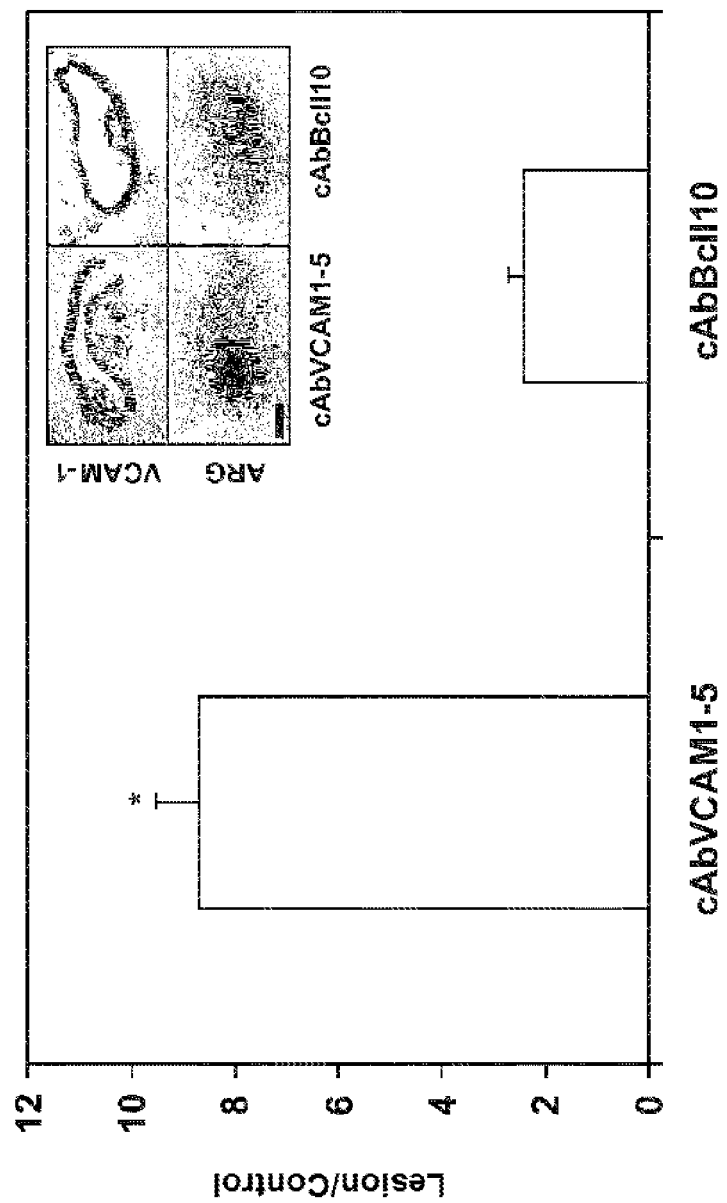
FIG. 5 illustrates histograms showing the lesion-to-control ratio obtained with the nanobody cAbVCAM1-5 and the control nanobody cAbBcII10 by quantification of the autoradiograms. *: $P<0.05$ versus cAbBcII10. Representative autoradiograms (ARG) obtained with $^{99m}$Tc-cAbVCAM1-5 and $^{99m}$Tc-cAbBcII10 on adjacent slides, in which VCAM-1 has further been immunolabeled (VCAM-1) are also shown at the top on the right of the figure. The scale bar represents 200 µm.

In the ApoE$^{-/-}$ mice, the inventors showed that aortic absorption of $^{99m}$Tc-cAbVCAM1-5 was in agreement with the extension index of the lesion. Indeed, the absorption of $^{99m}$Tc-cAbVCAM1-5 increased in the same time as the relative volume of the atherosclerotic lesion, while such a gradient was not observed with $^{99m}$Tc-cAbBcII10 (FIG. 4). The absorption of $^{99m}$Tc-cAbVCAM1-5 in the aorta was further characterised by autoradiography. As shown in FIG. 5, $^{99}$m Tc-cAbVCAM1-5 accumulated at the positive VCAM-1 atherosclerotic lesions, leading to a lesion-to-control ratio of 8.7±0.5 (p<0.05 versus cAbBcII10).

Stability—

Figure 6:
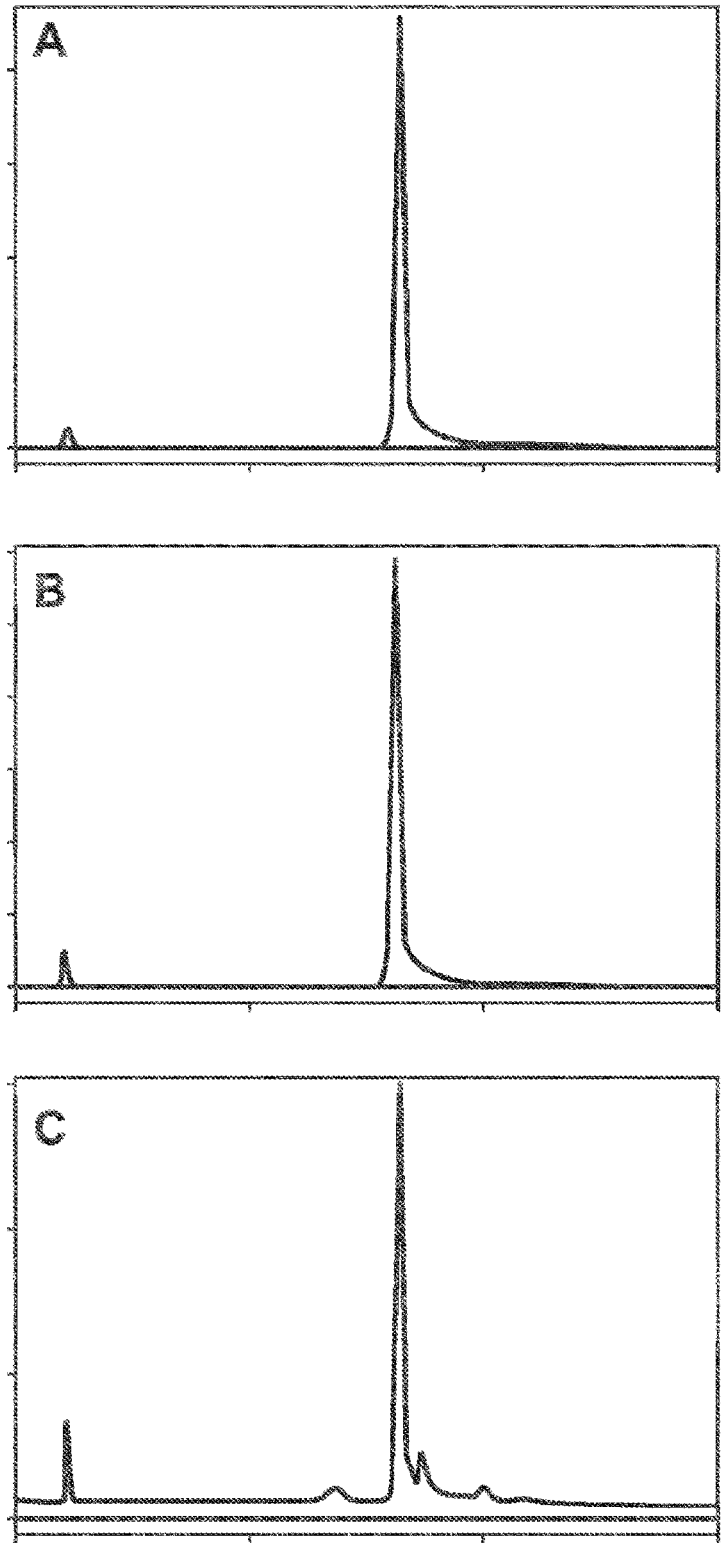
FIG. 6 illustrates the HPLC profiles of the $^{99m}$Tc-cAbVCAM1-5 nanobody showing that the nanobody is stable in vitro at 0 hours (A) and at 6 hours (B) after radiolabeling, as well as in vivo in the blood 3 hours after injection (C).

The inventors demonstrated with HPLC that $^{99m}$Tc-cAbVCAM1-5 was stable in vitro up to 6 hours after radiolabeling, and in vivo in blood 3 hours after injection, at the moment of SPECT imaging (FIG. 6).

Biodistribution in Controlled Mice—

Figure 7:
FIG. 7 illustrates the images of maximum intensity projections (MIP) of the $^{99m}$Tc-cAbBcII10 (A) and $^{99m}$Tc-cAbVCAM1-5 (B) control nanobodies obtained on an entire body with SPECT/CT in vivo 3 hours after intravenous injection in C57Bl/6J mice. The bladder (V), the kidneys (Re), the lymphatic ganglions (GL), the bone marrow (MO), the thymus (T) and the spleen (Ra) are indicated.

$^{99m}$Tc-cAbVCAM1-5 was rapidly removed from the blood stream and absorption in the kidneys, the spleen and the lymphoid tissues, was clearly identified on the SPECT images in vivo both in control mice C57Bl/6J and atherosclerotic mice ApoE$^{-/-}$, while only the kidneys and the bladder were visible after injecting $^{99m}$Tc-cAbBcII10 (FIG. 7). Absorption of $^{99m}$Tc-cAbVCAM1-5 in the lymphoid tissues of the control mice C57Bl/6J was further confirmed ex vivo by biodistribution analyses (Table 6).

TABLE 6

Biodistribution ex vivo of the nanobodies cAbVCAM1-5 and cAbBcll10 labelled with $^{99m}$Tc, 3 hours after injection into control mice C57Bl/6J.

| | C57Bl/6J | |
|---|---|---|
| | CAbVCAM1-5 | CAbBcll10 |
| Blood | 0.5 ± 0.1 | 0.4 ± 0.0 |
| Heart | 0.2 ± 0.0* | 0.1 ± 0.0 |
| Lung | 1.7 ± 0.2* | 0.8 ± 0.2 |
| Liver | 1.4 ± 0.2 | 1.0 ± 0.1 |
| Skeletal muscle | 0.1 ± 0.0 | 0.1 ± 0.0 |
| Skin | 0.4 ± 0.0 | 0.4 ± 0.0 |
| Fat | 0.2 ± 0.0 | 0.1 ± 0.0 |
| Brain | 0.0 ± 0.0* | 0.0 ± 0.0 |
| Salivary gland | 0.5 ± 0.0* | 0.3 ± 0.0 |
| Pancreas | 0.2 ± 0.0 | 0.2 ± 0.0 |
| Thyroid | 0.7 ± 0.1 | 0.5 ± 0.1 |
| Stomach | 0.5 ± 0.0* | 0.4 ± 0.0 |
| Bile | 0.3 ± 0.0 | 0.5 ± 0.1 |
| Intestine | 0.5 ± 0.1 | 0.3 ± 0.0 |
| Kidney | 287 ± 43 | 350 ± 16 |
| Urine | 59 ± 23 | 47 ± 8 |
| Spleen | 7.4 ± 0.2* | 0.3 ± 0.0 |
| Thymus | 1.5 ± 0.1* | 0.1 ± 0.0 |
| Bone marrow | 7.9 ± 2.0* | 0.4 ± 0.0 |

The results are shown as a mean ± mean standard error.
*P < 0.05 versus cAbBcll10.

Indeed, the inventors have shown that the absorption of $^{99m}$Tc-cAbVCAM1-5 represented 7.4±0.2, 1.5±0.1 and 7.9±2.0% ID/g in the spleen, the thymus and the bone marrow, respectively (p<0.05 versus $^{99m}$Tc-cAbBcII10 in the free tissues).

SPECT/CT Imaging—

Figure 8:
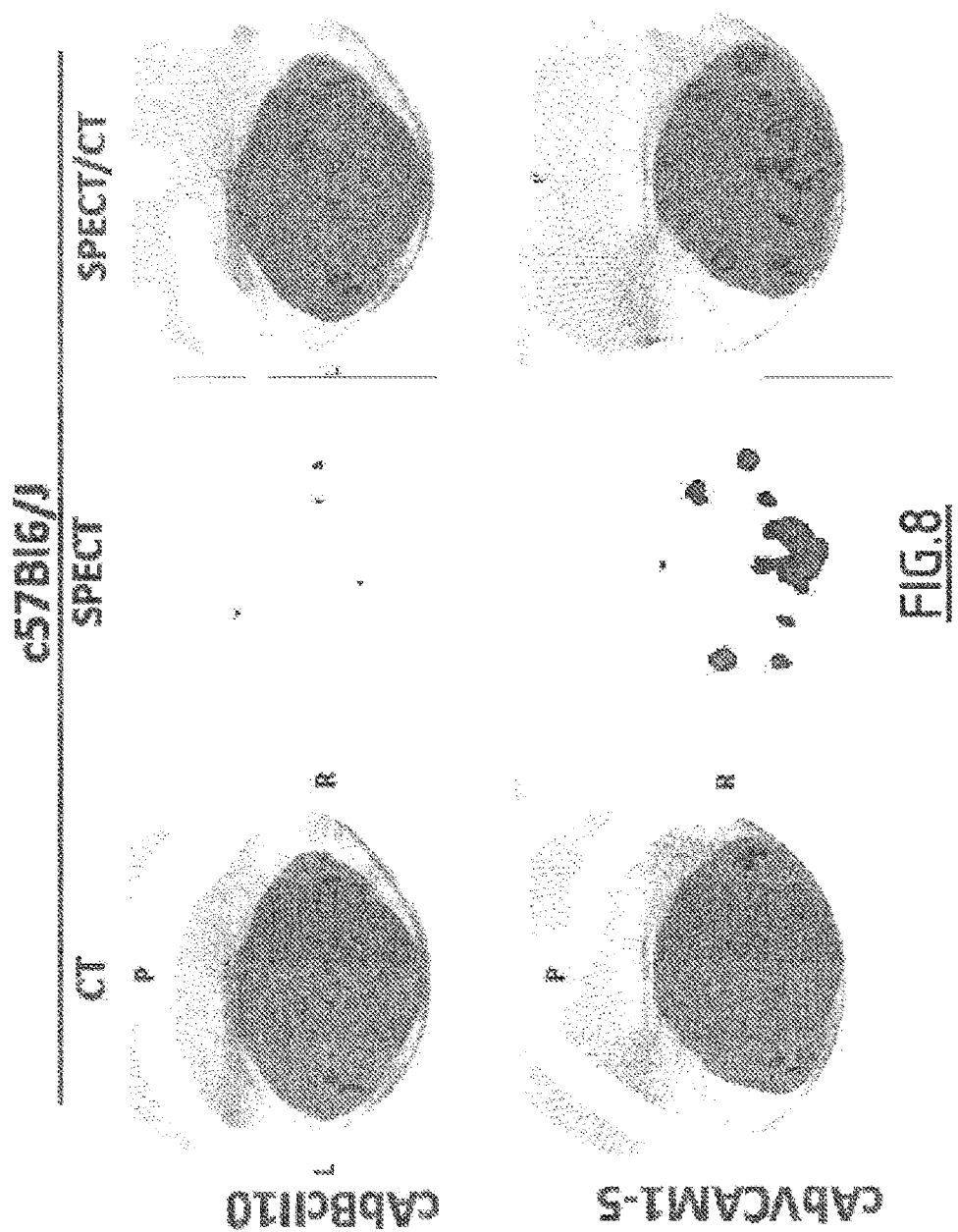
FIG. 8 illustrates representative coronary views in CT, SPECT and merging SPECT/CT imaging in vivo, taken at the aortic arch of C57Bl/6J mice, 3 hours after injecting the nanobodies $^{99m}$Tc-cAbBcII10 (cAbBcII10) or $^{99m}$Tc-cAbVCAM1-5 (cAbVCAM1-5). The scale of the SPECT images was adjusted from 1 to 3.4% of the injected dose so as to allow direct comparison. The axillary lymphatic ganglions (ln), the thymus (t) are indicated on the SPECT/CT images. The arrow indicates the aortic arch in the SPECT image. L represents the left, R represents the right, P represents the posterior face.
Figure 9:
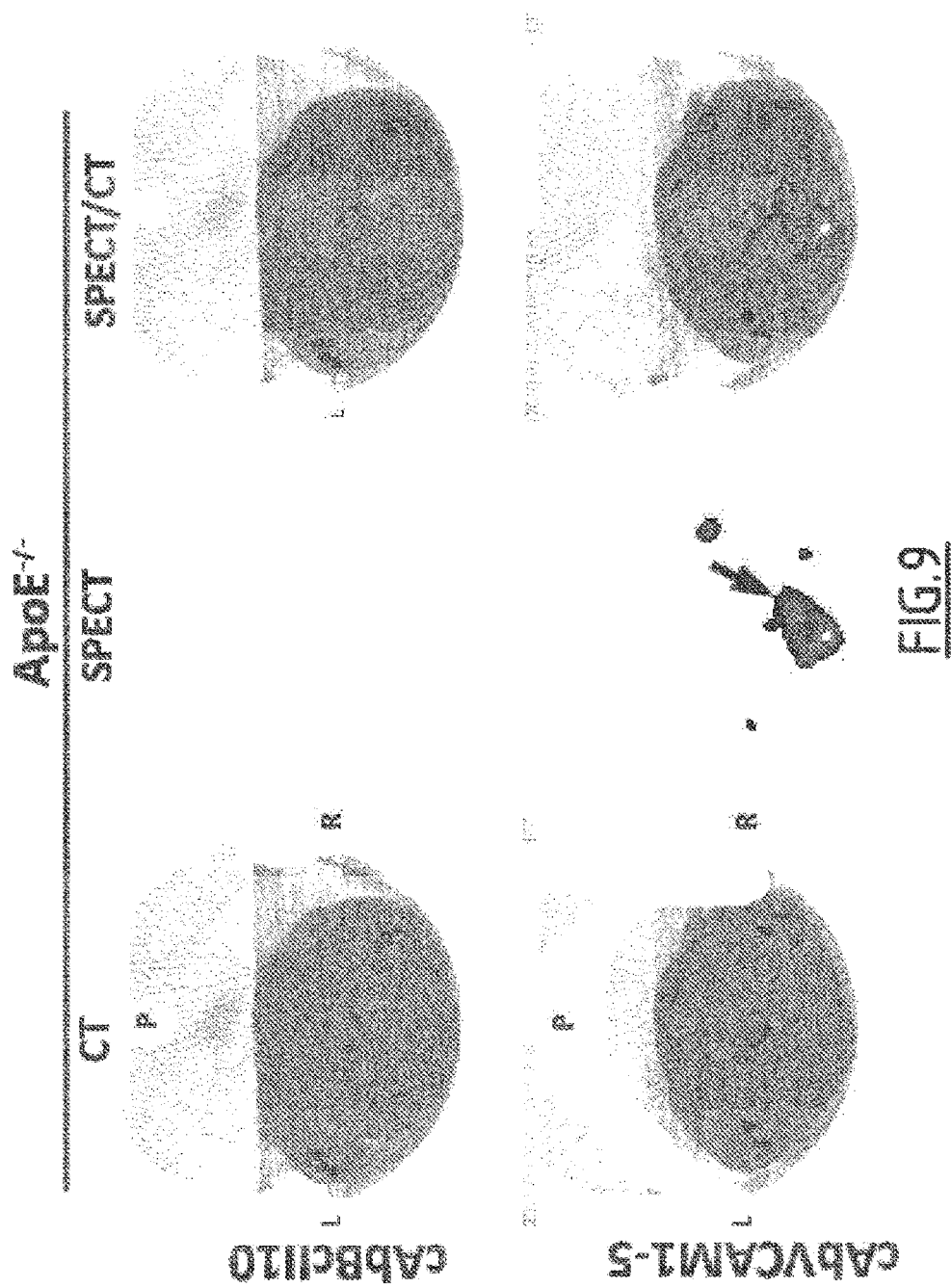
FIG. 9 illustrates representative coronary views in imaging by CT, SPECT and merging SPECT/CT in vivo, taken at the level of the aortic arch of ApoE$^{-/-}$ mice, 3 hours after injection of the nanobody $^{99m}$Tc-cAbBcII10 (cAbBcII10) or $^{99m}$Tc-cAbVCAM1-5 (cAbVCAM1-5). The scale of the SPECT images was adjusted from 1 to 3.4% of the injected dose so as to allow direct comparison. The axillary lymphatic ganglions (ln), the thymus (t) and the aortic arch (ao) are indicated on the SPECT/CT images. The arrow indicates the aortic arch in the SPECT image. L represents the left, R represents the right, P represents the posterior face.
Figure 10:
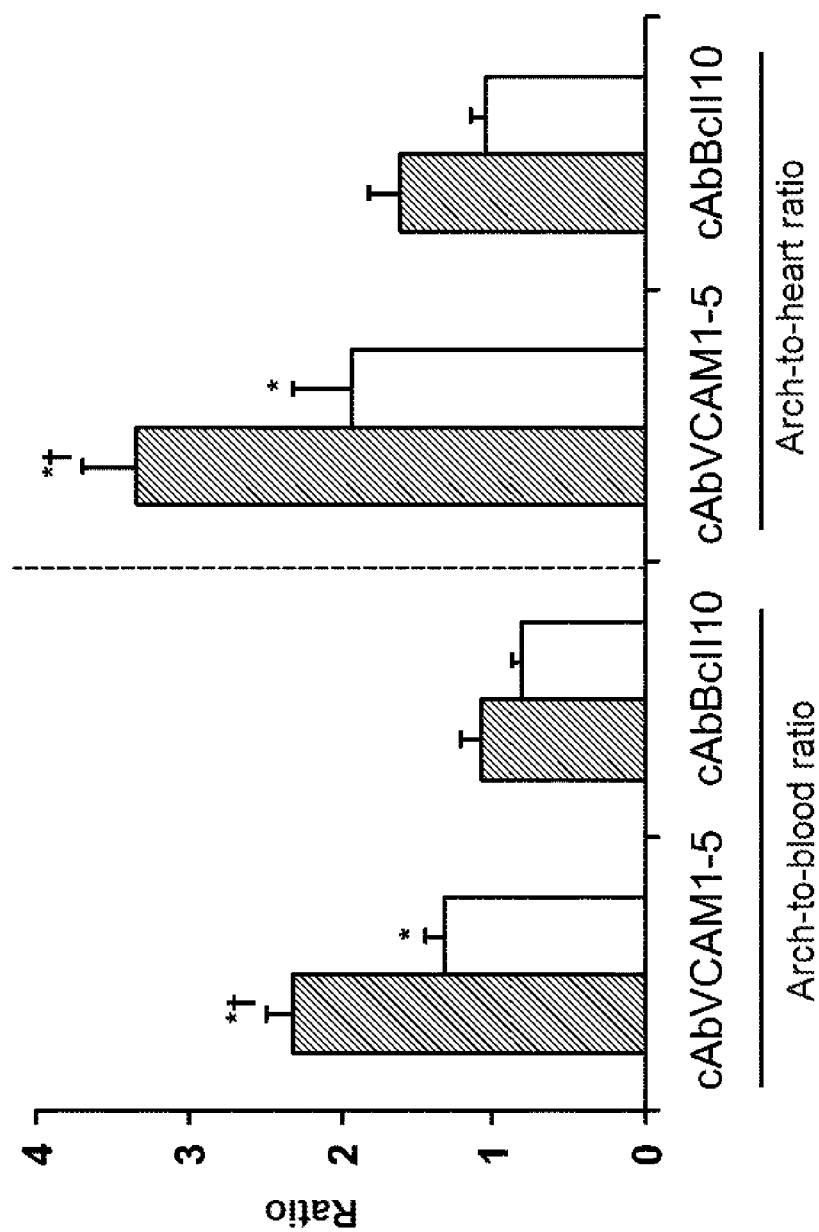
FIG. 10 illustrates histograms showing the arch-to-blood (left panel) and arch-to-heart (right panel) ratios in vivo, obtained on C57Bl/6J control mice (white bars) or on ApoE$^{-/-}$ mice (black bars) after administration of a control nanobody cAbBcII10 or of a nanobody cAbVCAM1-5, on the basis of quantifications of SPECT images. *: $P<0.05$ versus $^{99m}$Tc-AbBcII10. †: $P<0.05$ versus C57Bl/6J.

Subsequent to SPECT/CT imaging, the absorption of $^{99m}$Tc-cAbVCAM1-5 was viewed on atherosclerotic lesions of the aortic arch of ApoE$^{-/-}$ mice, while no absorption of tracer was observed in the same place in C57Bl/6J animals (FIGS. 8 and 9). Therefore, the arch-to-blood and arch-to-heart ratios prove to be significantly higher in ApoE$^{-/-}$ mice as compared with C57Bl/6J mice and as compared with the negative control nanobody (P<0.05; FIG. 10).

Reactivity of the Non-Radiolabelled Nanobodies Against Rabbit VCAM-1—

Figure 11:
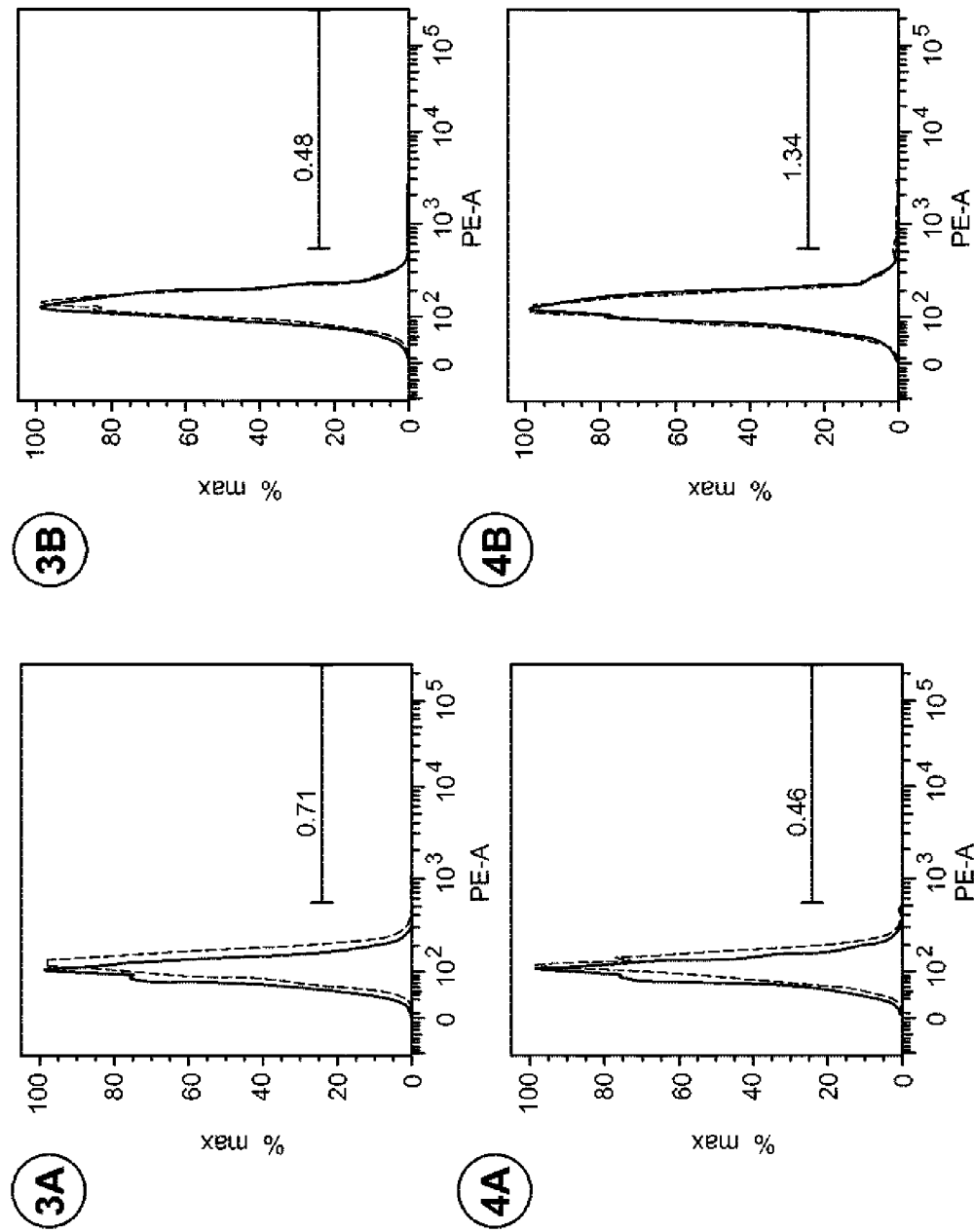
FIG. 11 illustrates the analysis by flow cytology of the anti-VCAM-1 nanobodies (cAbVCAM1-1: 1; cAbVCAM1-2: 2; cAbVCAM1-3: 3; cAbVCAM1-4: 4; cAbVCAM1-5: 5; cAbVCAM1-6: 6; cAbVCAM1-7: 7; cAbVCAM1-8: 8; cAbVCAM1-9: 9 and cAbVCAM1-10: 10) (dotted line) on non-transfected (A) CHO hamster cells or transfected (B) with a plasmid coding for rabbit VCAM-1. A condition without any nanobody was used as a negative control (solid line). These nanobodies cAbVCAM1-1 and cAbVCAM1-5 bind to the CHO cells expressing the rabbit VCAM-1.
Figure 11:
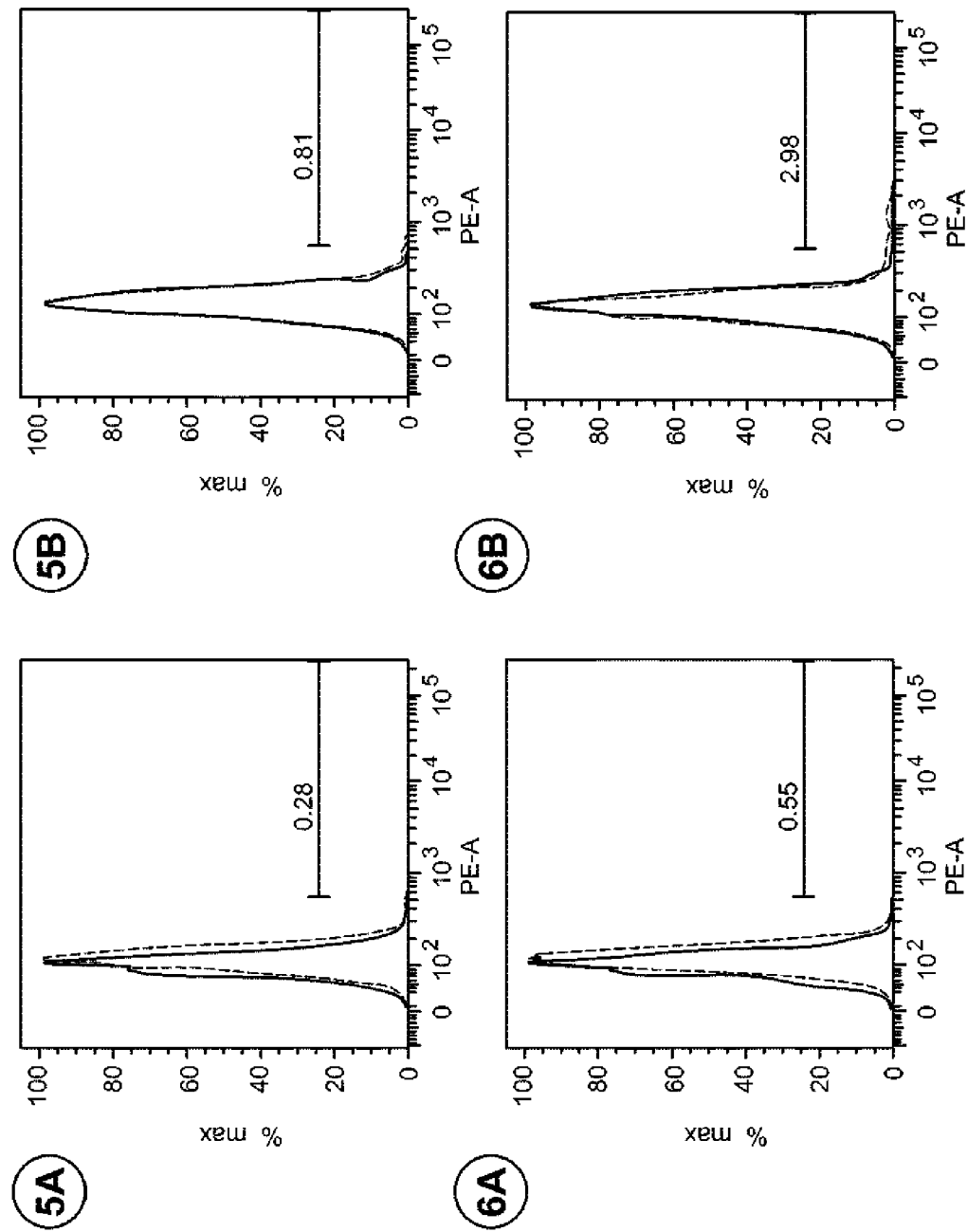
Figure 11:
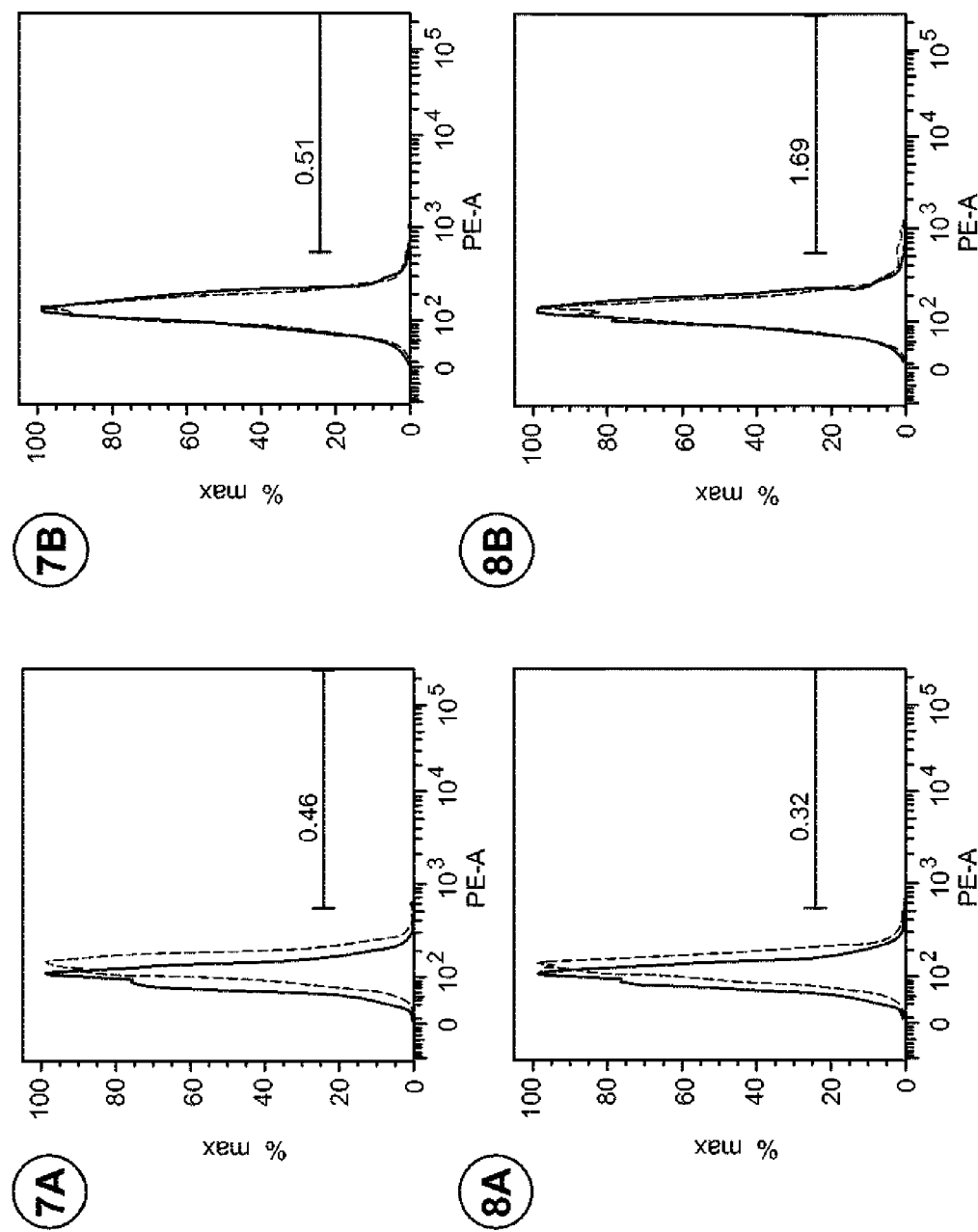
Figure 11:
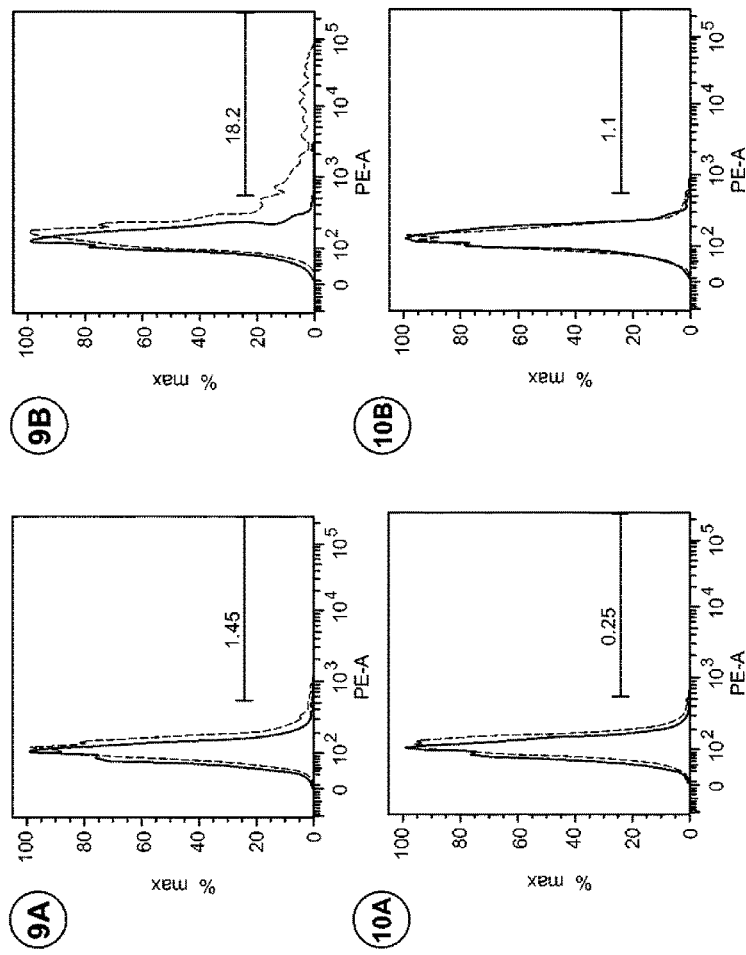

The inventors demonstrated by flow cytometry that cAbVCAM1-1 and cAbVCAM1-5 specifically bound to rabbit VCAM-1 (FIG. 11).

Discussion

This study was developed by the inventors for generating nanobodies recognizing both human and murine VCAM-1 homologs, to the extent that such cross-reactive ligands are of particular interest for transposition to clinical practice of the results validated on well characterized animal models. Ten anti-VCAM-1 nanobodies were generated and produced with affinities for the murine and/or human homologs of the order of one nanomolar, including 6 cross-reactive nanobodies. Further, two nanobodies, cAbVCAM1-1 and cAbVCAM1-5, are cross-reactive for rabbit VCAM-1. The high thermal resistance of the nanobodies, in particular of cAbVCAM1-5, gave the possibility of radiolabeling them with $^{99m}$Tc at 50° C. with high radiochemical purity (>95%). Further, the in vitro binding tests on positive VCAM-1 mouse endothelial cells reveal that these labeled nanobodies remained specific ligands of mVCAM1.

Because of their small size, the nanobodies have rapid blood clearance in vivo, resulting in an average circulation activity of 0.8% ID/g 3 hours, after injection into Apo$^{-/-}$ mice. Further, the background noise activity at the myocardium was also a minimum. In an important way, the absorption of the anti-VCAM-1 nanobodies at the aortic lesions was significantly higher than that of the negative control nanobody cAbBcII10, in particular for the nanobodies cAbVCAM1-5 and cAbVCAM1-3. Therefore, the lesion-to-control, lesion-to-blood and lesion-to-heart ratios were greater than 1, in particular for the nanobodies cAbVCAM1-5, cAbVCAM1-3, cAbVCAM1-8 and cAbVCAM1-9.

Absorption in Lymphoid Tissues

In addition to being absorbed in atherosclerotic lesions, the nanobodies according to the invention were also absorbed by lymphoid tissues, both in normal and hypercholesterolemic mice, as demonstrated by the biodistribution and SPECT imaging experiments. In particular, the three cross-reactive nanobodies with the strongest affinities for mVCAM-1 (cAbVCAM1-5/3/9) showed the strongest absorptions in the spleen and bone marrow. The constitutive expression of mVCAM-1 was observed by immunohistochemistry in the spleen, the bone marrow, the lymphatic ganglions and the thymus. Therefore, the binding of the anti-VCAM-1 nanobodies to lymphoid tissues was probably due to their specific binding to the VCAM-1 protein.

Selection of Compounds of Particular Interest

On the basis of the parameters summarized in Table 4, the nanobodies cAbVCAM1-5, cAbVCAM1-3, cAbVCAM1-8 and cAbVCAM1-9 were identified by the inventors as having particularly advantageous properties as compared with the other nanobodies, in particular with a view to use in medical imaging. The most promising nanobody is the nanobody cAbVCAM1-5. Indeed, cAbVCAM1-5 exhibits the highest lesion-to-control and lesion-to-heart ratios, as well as a strong lesion-to-blood ratio. Furthermore, it has good affinity both for human and murine VCAM-1 and has the highest thermal resistance and the highest production yield. Finally, cAbVCAM1-5 is cross-reactive for rabbit VCAM-1, a reference animal model in the study of atherosclerosis. cAbVCAM1-3 has the highest lesion-to-blood ratio and strong lesion-to-control and lesion-to-heart ratios. cAbVCAM1-8 has a particularly high lesion-to-heart ratio and the best affinity for human VCAM-1. Finally, cAbVCAM1-9 has the best incorporation at the atherosclerotic lesions and very good affinities for human and murine VCAM-1. Furthermore, AbVCAM1-5, AbVCAM1-3 and AbVCAM1-9 do not have any lysine at their CDRs, which is an advantage insofar that the presence of lysine may have a drawback for the coupling techniques allowing the nanobodies to be labeled by fluorescence or by radiolabeling, via their amine residues, with a view to PET imaging.

Imaging In Vivo of cAbVCAM1-5

$^{99m}$Tc-cAbVCAM1-5 is stable in vitro up to 6 hours after radiolabeling as well as in vivo in mouse blood, as demonstrated by HPLC. This gives the possibility of applying SPECT/CT imaging, 3 hours after injection. At this moment, the atherosclerotic lesions located at the aortic arch of ApoE$^{-/-}$ mice were successfully identified by the inventors with SPECT/CT imaging, with low background noise activities at the myocardium and at the blood. Autoradiography and immunohistochemistry confirmed that the aortic absorption of $^{99m}$Tc-cAbVCAM1-5 was focused in positive VCAM-1 atherosclerotic lesions. These experiments therefore show that $^{99m}$Tc-cAbVCAM1-5 is a suitable radiotracer for non-invasive in vivo imaging of inflammatory processes occurring at the atherosclerotic lesions.

Comparison with Other Radiotracers

Other radiotracers derived from antibodies were recently evaluated for imaging vulnerable atheroma plaques by using SPECT (Temma et al. (2010) *J. Nucl. Med.* 51:1979-1986; Kuge et al. (2010) *Eur. J. Nucl. Med. Mol. Imaging* 37:2093-2104). However, the low clearance of the entire antibodies leads to suboptimum target-to-background noise ratios, emphasizing the need for using antibody fragments. Among the other radiotracers evaluated earlier for SPECT or PET imaging of atherosclerotic lesions, $^{18}$FDG showed high absorption in macrophages, allowing in vivo imaging of carotid lesions in humans (Rudd et al. (2002) *Circulation* 105:2708-2711). However, because of the strong background noise at the myocardium, the imaging of coronary lesions remains very difficult in spite of the potential use of a specific diet intended to reduce absorption at the myocardium (Wykrzykowska et al. (2009) *J. Nucl. Med.* 50:563-568). Similarly, in an atherosclerosis mouse model, Laitinen et al. showed that the absorption at the myocardium of $^{18}$FDG was 18.13±10.59% ID/g relatively to 0.41±0.16% ID/g in atherosclerotic lesions, 1 hour after injection (Laitinen et al. (2006) *Eur. J. Nucl. Med. Mol. Imaging* 33:1461-1467).

CONCLUSION

The present inventors have thus identified and produced four anti-VCAM-1 nanobodies, cross-reactive for human VCAM-1, having important characteristics for use in medical imaging. The inventors in particular have directly shown that $^{99m}$Tc-cAbVCAM1-5 gave the possibility of successfully identifying atherosclerotic lesions in vivo by SPECT/CT imaging.

The invention claimed is:

1. A nanobody directed against VCAM-1 comprising:
   a) the amino acid sequences (i) YTNSIMYMA (SEQ ID NO: 1) as CDR1, (ii) AIRFPDDS (SEQ ID NO: 2) as CDR2 and (iii) RSSPYSFAWNDPSNYNY (SEQ ID NO: 3) as CDR3; or
   b) the amino acid sequences (i) FTYSSYYMS (SEQ ID NO: 4) as CDR1, (ii) GINVDGSN (SEQ ID NO: 5) as CDR2 and (iii) GSGRDSYDCYSGSWCP (SEQ ID NO: 6) as CDR3; or
   c) the amino acid sequences (i) FTFSNYYMT (SEQ ID NO: 7) as CDR1, (ii) RINSDGS (SEQ ID NO: 8) as CDR2 and (iii) GKSSV (SEQ ID NO: 9) as CDR3; or
   d) the amino acid sequences (i) FTFSSYYMS (SEQ ID NO: 10) as CDR1, (ii) GINVDGSN (SEQ ID NO: 11) as CDR2 and (iii) GSGRDSYDCYSGSWCP (SEQ ID NO: 12) as CDR3.

2. The nanobody according to claim 1, said nanobody comprising an amino acid sequence selected from the group consisting of the amino acid sequences SEQ ID NO: 13, SEQ ID NO: 14, SEQ ID NO: 15 and SEQ ID NO: 16.

3. The nanobody according to claim 1, said nanobody consisting of the amino acid sequence SEQ ID NO: 13.

4. The nanobody according to claim 1, said nanobody being associated with a detectable marker.

5. The nanobody according to claim 4, said detectable marker being a radionuclide.

6. An in vivo non-invasive medical imaging method comprising:
   administering the nanobody according to claim 4 to a patient, and
   detecting the nanobody in body areas of the patient.

7. A diagnostic or prognostic method of detecting an atheroma plaque in a patient comprising:
   administering to the patient a nanobody according to claim 4, and
   detecting the nanobody in a region of the atheroma plaque in the patient.

8. A method of administering a nanobody directed against VCAM-1 to a patient comprising;
   administering a therapeutically effective amount of the nanobody according to claim 1 to the patient.

9. An in vivo method of detecting VCAM-1 in a patient comprising:
    contacting the patient with the nanobody as defined in claim 4, and
    detecting the nanobody bound to VCAM-1 in the patient.

10. A pharmaceutical composition comprising a nanobody as defined in claim 1 in association with a pharmaceutically acceptable carrier.

11. The method according to claim 8, wherein the nanobody binds to and stabilizes an atheroma plaque.

12. The method according to claim 8, wherein the nanobody is coupled to a stabilizer of an atheroma plaque.

13. The method according to claim 12, wherein the stabilizer of an atheroma plaque is an anti-inflammatory molecule.

14. The method according to claim 13, wherein the anti-inflammatory molecule is a non-steroidal anti-inflammatory agent.

\* \* \* \* \*

SEQUENCE LISTING

<160> NUMBER OF SEQ ID NOS: 36

<210> SEQ ID NO 1
<211> LENGTH: 9
<212> TYPE: PRT
<213> ORGANISM: Artificial Sequence
<220> FEATURE:
<223> OTHER INFORMATION: CDR1 of cAbVCM1-5

<400> SEQUENCE: 1

Tyr Thr Asn Ser Ile Met Tyr Met Ala
1               5

<210> SEQ ID NO 2
<211> LENGTH: 8
<212> TYPE: PRT
<213> ORGANISM: Artificial Sequence
<220> FEATURE:
<223> OTHER INFORMATION: CDR2 of cAbVCAM1-5

<400> SEQUENCE: 2

Ala Ile Arg Phe Pro Asp Asp Ser
1               5

<210> SEQ ID NO 3
<211> LENGTH: 17
<212> TYPE: PRT
<213> ORGANISM: Artificial Sequence
<220> FEATURE:
<223> OTHER INFORMATION: CDR3 of cAbVCAM1-5

<400> SEQUENCE: 3

Arg Ser Ser Pro Tyr Ser Phe Ala Trp Asn Asp Pro Ser Asn Tyr Asn
1               5                   10                  15

Tyr

<210> SEQ ID NO 4
<211> LENGTH: 9
<212> TYPE: PRT
<213> ORGANISM: Artificial Sequence
<220> FEATURE:
<223> OTHER INFORMATION: CDR1 of cAbVCAM1-3

<400> SEQUENCE: 4

Phe Thr Tyr Ser Ser Tyr Tyr Met Ser
1               5

<210> SEQ ID NO 5
<211> LENGTH: 8
<212> TYPE: PRT
<213> ORGANISM: Artificial Sequence
<220> FEATURE:
<223> OTHER INFORMATION: CDR2 of cAbVCAM1-3

<400> SEQUENCE: 5

Gly Ile Asn Val Asp Gly Ser Asn
1               5

<210> SEQ ID NO 6
<211> LENGTH: 16
<212> TYPE: PRT
<213> ORGANISM: Artificial Sequence
<220> FEATURE:
<223> OTHER INFORMATION: CDR3 of cAbVCAM1-3

<400> SEQUENCE: 6

Gly Ser Gly Arg Asp Ser Tyr Asp Cys Tyr Ser Gly Ser Trp Cys Pro
1               5                   10                  15

<210> SEQ ID NO 7
<211> LENGTH: 9
<212> TYPE: PRT
<213> ORGANISM: Artificial Sequence
<220> FEATURE:
<223> OTHER INFORMATION: CDR1 of cAbVCAM1-8

<400> SEQUENCE: 7

Phe Thr Phe Ser Asn Tyr Tyr Met Thr
1               5

<210> SEQ ID NO 8
<211> LENGTH: 7
<212> TYPE: PRT
<213> ORGANISM: Artificial Sequence
<220> FEATURE:
<223> OTHER INFORMATION: CDR2 of cAbVCAM1-8

<400> SEQUENCE: 8

Arg Ile Asn Ser Asp Gly Ser
1               5

<210> SEQ ID NO 9
<211> LENGTH: 5
<212> TYPE: PRT
<213> ORGANISM: Artificial Sequence
<220> FEATURE:
<223> OTHER INFORMATION: CDR3 of cAbVCAM1-8

<400> SEQUENCE: 9

Gly Lys Ser Ser Val
1               5

<210> SEQ ID NO 10
<211> LENGTH: 9
<212> TYPE: PRT
<213> ORGANISM: Artificial Sequence
<220> FEATURE:
<223> OTHER INFORMATION: CDR1 of cAbVCAM1-9

<400> SEQUENCE: 10

Phe Thr Phe Ser Ser Tyr Tyr Met Ser
1               5

<210> SEQ ID NO 11
<211> LENGTH: 8
<212> TYPE: PRT
<213> ORGANISM: Artificial Sequence
<220> FEATURE:
<223> OTHER INFORMATION: CDR2 of cAbVCAM1-9

<400> SEQUENCE: 11

Gly Ile Asn Val Asp Gly Ser Asn
1               5

<210> SEQ ID NO 12
<211> LENGTH: 16
<212> TYPE: PRT
<213> ORGANISM: Artificial Sequence
<220> FEATURE:
<223> OTHER INFORMATION: CDR3 of cAbVCAM1-9

<400> SEQUENCE: 12

Gly Ser Gly Arg Asp Ser Tyr Asp Cys Tyr Ser Gly Ser Trp Cys Pro

<210> SEQ ID NO 13
<211> LENGTH: 126
<212> TYPE: PRT
<213> ORGANISM: Artificial Sequence
<220> FEATURE:
<223> OTHER INFORMATION: cAbVCAM1-5

<400> SEQUENCE: 13

Gln Val Gln Leu Gln Glu Ser Gly Gly Gly Ser Val Gln Thr Gly Gly
1               5                   10                  15

Ser Leu Arg Leu Ser Cys Ala Ala Ser Gly Tyr Thr Asn Ser Ile Met
            20                  25                  30

Tyr Met Ala Trp Phe Arg Gln Ala Pro Gly Lys Lys Arg Glu Gly Val
        35                  40                  45

Ala Ala Ile Arg Phe Pro Asp Asp Ser Ala Tyr Tyr Ala Gly Ser Val
    50                  55                  60

Lys Gly Arg Phe Thr Ile Ser His Asp Asn Ala Lys Asn Thr Val Tyr
65                  70                  75                  80

Leu Gln Met Asn Asn Leu Asn Pro Glu Asp Thr Ala Met Tyr Tyr Cys
                85                  90                  95

Ala Ala Arg Ser Ser Pro Tyr Ser Phe Ala Trp Asn Asp Pro Ser Asn
            100                 105                 110

Tyr Asn Tyr Trp Gly Gln Gly Thr Gln Val Thr Val Ser Ser
        115                 120                 125

<210> SEQ ID NO 14
<211> LENGTH: 125
<212> TYPE: PRT
<213> ORGANISM: Artificial Sequence
<220> FEATURE:
<223> OTHER INFORMATION: cAbVCAM1-3

<400> SEQUENCE: 14

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Tyr Ser Ser Tyr
            20                  25                  30

Tyr Met Ser Trp Val Arg Gln Ala Pro Gly Lys Gly Leu Glu Trp Val
        35                  40                  45

Ser Gly Ile Asn Val Asp Gly Ser Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Leu Tyr Tyr Cys
                85                  90                  95

Ala Thr Gly Ser Gly Arg Asp Ser Tyr Asp Cys Tyr Ser Gly Ser Trp
            100                 105                 110

Cys Pro Lys Gly Gln Gly Thr Gln Val Thr Val Ser Ser
        115                 120                 125

<210> SEQ ID NO 15
<211> LENGTH: 113
<212> TYPE: PRT
<213> ORGANISM: Artificial Sequence
<220> FEATURE:
<223> OTHER INFORMATION: cAbVCAM1-8

<400> SEQUENCE: 15

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Thr Trp Val Arg Arg Ala Pro Gly Lys Gly Leu Glu Trp Val
                35                  40                  45

Ser Arg Ile Asn Ser Asp Gly Ser Thr Leu Tyr Leu Pro Ser Val Lys
        50                  55                  60

Gly Arg Phe Thr Ile Ser Arg Asp Asn Ala Lys Asn Thr Leu Tyr Leu
65              70                  75                  80

Gln Met Asn Ser Leu Lys Ser Glu Asp Thr Gly Trp Tyr Tyr Cys Val
                85                  90                  95

Glu Gly Lys Ser Ser Val Arg Gly Gln Gly Thr Gln Val Thr Val Ser
            100                 105                 110

Ser

<210> SEQ ID NO 16
<211> LENGTH: 125
<212> TYPE: PRT
<213> ORGANISM: Artificial Sequence
<220> FEATURE:
<223> OTHER INFORMATION: cAbVCAM1-9

<400> SEQUENCE: 16

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
                35                  40                  45

Ser Gly Ile Asn Val Asp Gly Ser Asn Thr Tyr Tyr Ala Asp Ser Val
        50                  55                  60

Lys Gly Arg Phe Thr Ile Ser Arg Asp Asn Ala Lys Asn Thr Leu Tyr
65              70                  75                  80

Leu Gln Met Asn Ser Leu Lys Ser Glu Asp Thr Ala Leu Tyr Tyr Cys
                85                  90                  95

Ala Thr Gly Ser Gly Arg Asp Ser Tyr Asp Cys Tyr Ser Gly Ser Trp
            100                 105                 110

Cys Pro Lys Gly Gln Gly Thr Gln Val Thr Val Ser Ser
        115                 120                 125

<210> SEQ ID NO 17
<211> LENGTH: 26
<212> TYPE: PRT
<213> ORGANISM: Artificial Sequence
<220> FEATURE:
<223> OTHER INFORMATION: FR1 of cAbVCAM1-5

<400> SEQUENCE: 17

Gln Val Gln Leu Gln Glu Ser Gly Gly Gly Ser Val Gln Thr Gly Gly
1               5                   10                  15

Ser Leu Arg Leu Ser Cys Ala Ala Ser Gly
            20                  25

<210> SEQ ID NO 18
<211> LENGTH: 14
<212> TYPE: PRT
<213> ORGANISM: Artificial Sequence -continued

```
<220> FEATURE:
<223> OTHER INFORMATION: FR2 of cAbVCAM1-5

<400> SEQUENCE: 18

Trp Phe Arg Gln Ala Pro Gly Lys Lys Arg Glu Gly Val Ala
1               5                   10

<210> SEQ ID NO 19
<211> LENGTH: 41
<212> TYPE: PRT
<213> ORGANISM: Artificial Sequence
<220> FEATURE:
<223> OTHER INFORMATION: FR3 of cAbVCAM1-5

<400> SEQUENCE: 19

Ala Tyr Tyr Ala Gly Ser Val Lys Gly Arg Phe Thr Ile Ser His Asp
1               5                   10                  15

Asn Ala Lys Asn Thr Val Tyr Leu Gln Met Asn Asn Leu Asn Pro Glu
            20                  25                  30

Asp Thr Ala Met Tyr Tyr Cys Ala Ala
        35                  40

<210> SEQ ID NO 20
<211> LENGTH: 11
<212> TYPE: PRT
<213> ORGANISM: Artificial Sequence
<220> FEATURE:
<223> OTHER INFORMATION: FR4 of cAbVCAM1-5

<400> SEQUENCE: 20

Trp Gly Gln Gly Thr Gln Val Thr Val Ser Ser
1               5                   10

<210> SEQ ID NO 21
<211> LENGTH: 26
<212> TYPE: PRT
<213> ORGANISM: Artificial Sequence
<220> FEATURE:
<223> OTHER INFORMATION: FR1 of cAbVCAM1-3

<400> SEQUENCE: 21

Gln Val Gln Leu Gln Glu Ser Gly Gly Gly Ser Val Gln Ala Gly Gly
1               5                   10                  15

Ser Leu Arg Leu Ser Cys Thr Ala Ser Gly
            20                  25

<210> SEQ ID NO 22
<211> LENGTH: 14
<212> TYPE: PRT
<213> ORGANISM: Artificial Sequence
<220> FEATURE:
<223> OTHER INFORMATION: FR2 of cAbVCAM1-3

<400> SEQUENCE: 22

Trp Val Arg Gln Ala Pro Gly Lys Gly Leu Glu Trp Val Ser
1               5                   10

<210> SEQ ID NO 23
<211> LENGTH: 41
<212> TYPE: PRT
<213> ORGANISM: Artificial Sequence
<220> FEATURE:
<223> OTHER INFORMATION: FR3 of cAbVCAM1-3

<400> SEQUENCE: 23
```

```
Thr Tyr Tyr Ala Asp Ser Val Lys Gly Arg Phe Thr Ile Ser Arg Asp
 1               5                  10                  15

Asn Ala Lys Asn Thr Leu Tyr Leu Gln Met Asn Ser Leu Lys Ser Glu
            20                  25                  30

Asp Thr Ala Leu Tyr Tyr Cys Ala Thr
        35                  40

<210> SEQ ID NO 24
<211> LENGTH: 11
<212> TYPE: PRT
<213> ORGANISM: Artificial Sequence
<220> FEATURE:
<223> OTHER INFORMATION: FR4 of cAbVCAM1-3

<400> SEQUENCE: 24

Lys Gly Gln Gly Thr Gln Val Thr Val Ser Ser
 1               5                  10

<210> SEQ ID NO 25
<211> LENGTH: 26
<212> TYPE: PRT
<213> ORGANISM: Artificial Sequence
<220> FEATURE:
<223> OTHER INFORMATION: FR1 of cAbVCAM1-8

<400> SEQUENCE: 25

Gln Val Gln Leu Gln Glu Ser Gly Gly Gly Leu Val Gln Pro Gly Gly
 1               5                  10                  15

Ser Leu Arg Leu Ser Cys Ala Ala Ser Gly
            20                  25

<210> SEQ ID NO 26
<211> LENGTH: 14
<212> TYPE: PRT
<213> ORGANISM: Artificial Sequence
<220> FEATURE:
<223> OTHER INFORMATION: FR2 of cAbVCAM1-8

<400> SEQUENCE: 26

Trp Val Arg Arg Ala Pro Gly Lys Gly Leu Glu Trp Val Ser
 1               5                  10

<210> SEQ ID NO 27
<211> LENGTH: 41
<212> TYPE: PRT
<213> ORGANISM: Artificial Sequence
<220> FEATURE:
<223> OTHER INFORMATION: FR3 of cAbVCAM1-8

<400> SEQUENCE: 27

Thr Leu Tyr Leu Pro Ser Val Lys Gly Arg Phe Thr Ile Ser Arg Asp
 1               5                  10                  15

Asn Ala Lys Asn Thr Leu Tyr Leu Gln Met Asn Ser Leu Lys Ser Glu
            20                  25                  30

Asp Thr Gly Trp Tyr Tyr Cys Val Glu
        35                  40

<210> SEQ ID NO 28
<211> LENGTH: 11
<212> TYPE: PRT
<213> ORGANISM: Artificial Sequence
<220> FEATURE:
<223> OTHER INFORMATION: FR4 of cAbVCAM1-8

<400> SEQUENCE: 28
```

Arg Gly Gln Gly Thr Gln Val Thr Val Ser Ser
1               5                   10

<210> SEQ ID NO 29
<211> LENGTH: 26
<212> TYPE: PRT
<213> ORGANISM: Artificial Sequence
<220> FEATURE:
<223> OTHER INFORMATION: FR1 of cAbVCAM1-9

<400> SEQUENCE: 29

Gln Val Gln Leu Gln Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 30
<211> LENGTH: 14
<212> TYPE: PRT
<213> ORGANISM: Artificial Sequence
<220> FEATURE:
<223> OTHER INFORMATION: FR2 of cAbVCAM1-9

<400> SEQUENCE: 30

Trp Val Arg Gln Ala Pro Gly Lys Gly Leu Glu Trp Val Ser
1               5                   10

<210> SEQ ID NO 31
<211> LENGTH: 41
<212> TYPE: PRT
<213> ORGANISM: Artificial Sequence
<220> FEATURE:
<223> OTHER INFORMATION: FR3 of cAbVCAM1-9

<400> SEQUENCE: 31

Thr Tyr Tyr Ala Asp Ser Val Lys Gly Arg Phe Thr Ile Ser Arg Asp
1               5                   10                  15

Asn Ala Lys Asn Thr Leu Tyr Leu Gln Met Asn Ser Leu Lys Ser Glu
            20                  25                  30

Asp Thr Ala Leu Tyr Tyr Cys Ala Thr
        35                  40

<210> SEQ ID NO 32
<211> LENGTH: 11
<212> TYPE: PRT
<213> ORGANISM: Artificial Sequence
<220> FEATURE:
<223> OTHER INFORMATION: FR4 of cAbVCAM1-9

<400> SEQUENCE: 32

Lys Gly Gln Gly Thr Gln Val Thr Val Ser Ser
1               5                   10

<210> SEQ ID NO 33
<211> LENGTH: 132
<212> TYPE: PRT
<213> ORGANISM: Artificial Sequence
<220> FEATURE:
<223> OTHER INFORMATION: cAbVCAM1-5 6His

<400> SEQUENCE: 33

Gln Val Gln Leu Gln Glu Ser Gly Gly Gly Ser Val Gln Thr Gly Gly
1               5                   10                  15

Ser Leu Arg Leu Ser Cys Ala Ala Ser Gly Tyr Thr Asn Ser Ile Met

```
                 20                  25                  30

Tyr Met Ala Trp Phe Arg Gln Ala Pro Gly Lys Lys Arg Glu Gly Val
            35                  40                  45

Ala Ala Ile Arg Phe Pro Asp Asp Ser Ala Tyr Tyr Ala Gly Ser Val
        50                  55                  60

Lys Gly Arg Phe Thr Ile Ser His Asp Asn Ala Lys Asn Thr Val Tyr
65                  70                  75                  80

Leu Gln Met Asn Asn Leu Asn Pro Glu Asp Thr Ala Met Tyr Tyr Cys
                85                  90                  95

Ala Ala Arg Ser Ser Pro Tyr Ser Phe Ala Trp Asn Asp Pro Ser Asn
            100                 105                 110

Tyr Asn Tyr Trp Gly Gln Gly Thr Gln Val Thr Val Ser Ser His His
        115                 120                 125

His His His His
        130

<210> SEQ ID NO 34
<211> LENGTH: 131
<212> TYPE: PRT
<213> ORGANISM: Artificial Sequence
<220> FEATURE:
<223> OTHER INFORMATION: cAbVCAM1-3 6His

<400> SEQUENCE: 34

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Tyr Ser Ser Tyr
            20                  25                  30

Tyr Met Ser Trp Val Arg Gln Ala Pro Gly Lys Gly Leu Glu Trp Val
            35                  40                  45

Ser Gly Ile Asn Val Asp Gly Ser Asn Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Leu Tyr Tyr Cys
                85                  90                  95

Ala Thr Gly Ser Gly Arg Asp Ser Tyr Asp Cys Tyr Ser Gly Ser Trp
            100                 105                 110

Cys Pro Lys Gly Gln Gly Thr Gln Val Thr Val Ser Ser His His His
            115                 120                 125

His His His
        130

<210> SEQ ID NO 35
<211> LENGTH: 119
<212> TYPE: PRT
<213> ORGANISM: Artificial Sequence
<220> FEATURE:
<223> OTHER INFORMATION: cAbVCAM1-8 6His

<400> SEQUENCE: 35

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Thr Trp Val Arg Arg Ala Pro Gly Lys Gly Leu Glu Trp Val
            35                  40                  45
```

```
Ser Arg Ile Asn Ser Asp Gly Ser Thr Leu Tyr Leu Pro Ser Val Lys
    50              55                  60

Gly Arg Phe Thr Ile Ser Arg Asp Asn Ala Lys Asn Thr Leu Tyr Leu
65              70                  75                      80

Gln Met Asn Ser Leu Lys Ser Glu Asp Thr Gly Trp Tyr Tyr Cys Val
            85                  90                  95

Glu Gly Lys Ser Ser Val Arg Gly Gln Gly Thr Gln Val Thr Val Ser
                100                 105             110

Ser His His His His His His
        115

<210> SEQ ID NO 36
<211> LENGTH: 131
<212> TYPE: PRT
<213> ORGANISM: Artificial Sequence
<220> FEATURE:
<223> OTHER INFORMATION: cAbVCAM1-9 6His

<400> SEQUENCE: 36

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
            35                  40                  45

Ser Gly Ile Asn Val Asp Gly Ser Asn Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Leu Tyr Tyr Cys
                85                  90                  95

Ala Thr Gly Ser Gly Arg Asp Ser Tyr Asp Cys Tyr Ser Gly Ser Trp
                100                 105                 110

Cys Pro Lys Gly Gln Gly Thr Gln Val Thr Val Ser Ser His His His
            115                 120                 125

His His His
        130
```